US007358224B2

(12) United States Patent
Bishop

(10) Patent No.: US 7,358,224 B2
(45) Date of Patent: Apr. 15, 2008

(54) CLASS III SLRP AGONISTS FOR THE REDUCTION OF BLOOD VESSEL FORMATION

(75) Inventor: Paul N. Bishop, Manchester (GB)

(73) Assignee: The University of Manchester, Manchester (GB)

( * ) Notice: Subject to any disclaimer, the term of this patent is extended or adjusted under 35 U.S.C. 154(b) by 57 days.

(21) Appl. No.: 10/558,606

(22) PCT Filed: May 28, 2004

(86) PCT No.: PCT/GB2004/002269

§ 371 (c)(1),
(2), (4) Date: Nov. 29, 2005

(87) PCT Pub. No.: WO2004/105784

PCT Pub. Date: Dec. 9, 2004

(65) Prior Publication Data

US 2007/0021334 A1 Jan. 25, 2007

(30) Foreign Application Priority Data

May 29, 2003 (GB) ................................ 0312292.6
Jan. 12, 2004 (GB) ................................ 0400547.6

(51) Int. Cl.
*C07K 14/00* (2006.01)

(52) U.S. Cl. .......................................... 514/2; 530/350

(58) Field of Classification Search .................... 514/2; 530/300, 350
See application file for complete search history.

(56) References Cited

U.S. PATENT DOCUMENTS

| | | | |
|---|---|---|---|
| 6,413,931 | B1 | 7/2002 | Yang et al. |
| 2002/0115589 | A1 | 8/2002 | Nixon et al. |
| 2003/0148351 | A1 | 8/2003 | Mayne et al. |

FOREIGN PATENT DOCUMENTS

| | | |
|---|---|---|
| DE | 4445630 | 6/1996 |
| WO | WO 97/15330 | 5/1997 |
| WO | WO 98/13071 | 4/1998 |
| WO | WO 98/24466 | 6/1998 |
| WO | WO 01/19386 | 3/2001 |

OTHER PUBLICATIONS

Canfield, A.E. et al., "Evidence that tenascin and thrombospondin-1 modulate sprouting of endothelial cells," J. Cell Sci. (1995) 108:797-809.

Friedman, J.S. et al., "Protein localization in the human eye and genetic screen of opticin," Human Mol. Genet. (2002) 11(11):1333-1342.

Le Goff et al., "Characterization of opticin and evidence of stable dimerisation in solution," J. Biol. Chem. (2003) 278:45280-45287.

Pellegrini, B. et al., "Cloning and characterization of opticin cDNA: evaluation as a candidate for canine oculo-skeletal dysplasia," Gene (2002) 282:121-131.

Slevin, M. et al., "Angiogenic oligosaccharides of hyaluronan induce multiple signaling pathways affecting vascular endothelial cell mitogenic and wound healing responses," J. Biol. Chem. (2002) 277:41046-41059.

Stander, M. et al., "Transforming growth factor-beta and p-21 : multiple molecular targets of decorin-mediated suppression of neoplastic growth," Cell Tiss. Res. (1999) 296(2):221-227.

Tasheva, E.S., "Analysis of the promoter region of human mimecan gene," Biochimica et Biophysica Acta (2002) 1575(1-3):123-129.

Tralhao, J.G. et al., "In vivo selective and distant killing of cancer cells using adenovirus-mediated decorin gene transfer," The FASEB Journal (Jan. 2003) 17(3):464-466.

Vuillermoz, B. et al., "The small leucine-rich proteoglycan lumican inhibits melanoma progression," Exp. Cell Res. (2004) 296(2):294-306.

*Primary Examiner*—Karen Cochrane Carlson
(74) *Attorney, Agent, or Firm*—Michael Best & Friedrich LLP

(57) ABSTRACT

The invention relates to the use of an agent that promotes class III SLRP activity in the manufacture of a medicament for the inhibition of blood vessel formation. In addition the invention relates to the use of an agent that promotes class III SLRP activity in the manufacture of a medicament for the prevention and/or treatment of conditions characterised by excessive activity and/or migration of monocytes and/or macrophages. Suitable agents may include class III SLRPs such as opticin. Methods of treatment using agents able to promote class III SLRP activity are also provided.

10 Claims, 13 Drawing Sheets

Figure 1. Mature protein sequences

Human opticin:

ASLPRKERKRREEQMPREGDSFEVLPLRNDVLNPDNYGEVIDLSNYEELTDYGDQLPEVKVTSLA
PATSISPAKSTTAPGTPSSNPTMTRPTTAGLLLSSQPNHGLPTCLVCVCLGSSVYCDDIDLEDIP
PLPRRTAYLYARFNRISRIRAEDFKGLTKLKRIDLSNNLISSIDNDAFRLLHALQDLILPENQLE
ALPVLPSGIEFLDVRLNRLQSSGIQPAAFRAMEKLQFLYLSDNLLDSIPGPLPLSLRSVHLQNNL
IETMQRDVFCDPEEHKHTRRQLEDIRLDGNPINLSLFPSAYFCLPRLPIGRFT

Bovine opticin:

ASLSEEREGDPYAILHLGDYVLSLDNYDEVIDPSNYDELIDYGDQLPQVKGTSLASLTRTRFTQS
TEAARTLPSNPTTARPPTLGLLAAPANHGLPTCLICVCLGSSVYCDDADLENIPPLPQTTAYLYA
RFNRISHIRAGDFKGLTKLKRIDLSGNSISSIDDKALRLLPALRDLILPENKLVALPTLPTSIEV
LDVRMNRLQSSGIQPEAFRALEKLQFLYLADNLLDAIPPSLPLSLRSLHLQNNMIETMQRDAFCD
AEEHRHTRRPLEDIRLDGNPINLSLFPSAYFCLPRLPTGRFV

Human epiphycan:

APTLESINYDSETYDATLEDLDNLYNYENIPVGKVEIEIATVMPSGNRELLTPPPQPEKAQEEEE
EEESTPRLIDGSSPQEPEFTGVLGPHTNEDFPTCLLCTCISTTVYCDDHELAIPPLPKNTAYFYS
RFNRIKKINKNDFASLSDLKRIDLTSNLISEIDEDAFRKLPQLRELVLRDNKIRQELPTTLTFID
ISNNRLGRKGIKQEAFKDMYDLHHLYLTDNNLDHIPLPLPENLRALHLQNNNILEMHEDTFCNVK
NLTYIRKALEDIRLDGNPINLSKTPQAYMCLPRLPVGSLV

Human osteoglycin/mimecan:

KPAPPTQQDSRIIYDYGTDNFEESIFSQDYEDKYLDGKNIKEKETVIIPNEKSLQLQKDEAITPL
PPKKENDEMPTCLLCVCLSGSVYCEEVDIDAVPPLPKESAYLYARFNKIKKLTAKDFADIPNLRR
LDFTGNLIEDIEDGTFSKLSLLEELSLAENQLLKLPVLPPKLTLFNAKYNKIKSRGIKANAFKKL
NNLTFLYLDHNALESVPLNLPESLRVIHLQFNNIASITDDTFCKANDTSYIRDRIEEIRLEGNPI
VLGKHPNSFICLKRLPIGSYF

Alignment of leucine-rich repeat regions of opticin, osteoglycin/mimecan and epiphycan:

```
Opticin       GLPTCLVCVCLGSSVYCDDIDLEDIPPLPRRTAYLYARFNRISRIRAEDFKGLTKLKRID
Epiphycan     DFPTCLWCTCISTTVYCDDHELDAIPPLPKNTAYFYSRFNRIKKINKNDFASLSDLKRID
Osteoglycin   EMPTCLLCVCLSGSVYCEEVDIDAVPPLPKESAYLYARFNKIKKLTAKDFADIPNLRRLD
               :**** *.*:. :***:: ::: :****:.:**:*:***:*.::  :** .:..*:*:*

Opticin       LSNNLISSIDNDAFRLLHALQDLILPENQLEALPVLPSGIEFLDVRLNRLQSSGIQPAAF
Epiphycan     LTSNLISEIDEDAFRKLPQLRELVLRDNKIRQLPELPTTSTFIDISNNRLGRKGIKQEAF
Osteoglycin   FTGNLIEDIEDGTFSKLSLLEELSLAENQLLKLPVLPPKLTLFNAKYNKIKSRGIKANAF
              ::.***..*::.:*  *  *.:* * :*::  ** **.   :::   *::   **:  **

Opticin       RAMEKLQFLYLSDNLLDSIPGPLPLSLRSVHLQNNLIETMQRDVFCDPEEHKHTRRQLED
Epiphycan     KDMYDLHHLYLTDNNLDHIPLPLPENLRALHLQNNNILEMHEDTFCNGKNLTYIRKALED
Osteoglycin   KKLNNLTFLYLDHNALESVPLNLPESLRVIHLQFNNIASITDDTFCKANDTSYIRDRIEE
              : : .* .*** .* *: :*  ** .** :*** * *  :  *.**. :: .: *  :*:

Opticin       IRLDGNPINLSLFPSAYFCLPRLPIGRFT
Epiphycan     IRLDGNPINLSKTPQAYMCLPRLPVGSLV
Osteoglycin   IRLEGNPIVLGKHPNSFICLKRLPIGSYF
              ***:**** *.  *.:::** ***:*
```

* = Identical amino acids across all three proteins
: = Conserved amino acids
. = Semi-conserved amino acids

ASLSEEREGDPYAILHLGDYVLSLDNYDEVIDPSNYDELIDYGDQLPQVKGTSLASLTRT
RFTQSTEAARTLPSNPTTARPPTLGLL

Fig 2b

```
Human:   DNYGEVIDLSNYEELTDYGDQLPE
Bovine:  DNYDEVIDPSNYDELIDYGDQLPQ
```

Fig 2c

Alignment of NH terminal opticin sequences from different species:

```
Bovine  ASLS--EERE---------GDPYAILHLGDYVLSLDNYDEVIDPSNYDELIDYGDQLPQVKG
Dog     ASLP--KERKRRDEMH---GEGDSYVVLGNYVLGPDNYDEVIDLSDYEGLMDYGDQLPEAKV
Human   ASLPR-KERKRREEQMPREGDSFEVLPLRNDVLNPDNYGEVIDLSNYEELTDYGDQLPEVKV
Mouse   ASLLGEREREEQSPEE---GDTYASLYVGNHTLSIEDYNEVIDLSNYEELADYGDQIPEAKI
        ***   .**:         *:    : : : .*. ::*.**** *:*: * *****:*:.*.

Bovine            TSLASLTRTRFTQSTEAARTLPSNPTTARPPTLGLLAAP 109
Dog               TNLAPPTGISSAQSTMTPRTLSLKPTMIRPTELGVLGSP 115
Human             TSLAPATSISPAKSTTAPGTTSSNPTMTRPTTAGLLLSS 119
Mouse             SNLTLPTRTSPT-STVAQKTLSPNLTMAVPTTTGLLNSQ 116
                  :.*:  *    : ** :  * . : *   *.  *:* :
```

Figure 3. Proliferation assays with FGF-2
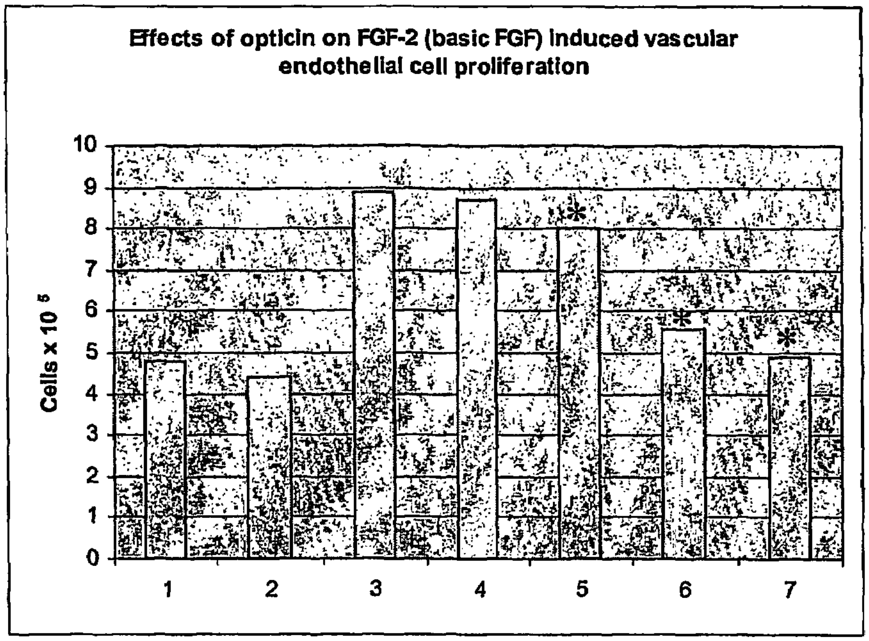
1 = Control
2 = Control with added opticin (10 μg/ml)
3 = FGF-2 alone
4 = FGF-2 and 0.1 μg/ml opticin
5 = FGF-2 and 1 μg/ml opticin
6 = FGF-2 and 10 μg/ml opticin
7 = FGF-2 and 25 μg/ml opticin
* Denotes significant decrease in proliferation
Figure 4 Proliferation assays comparing FGF-2 and FGF-1
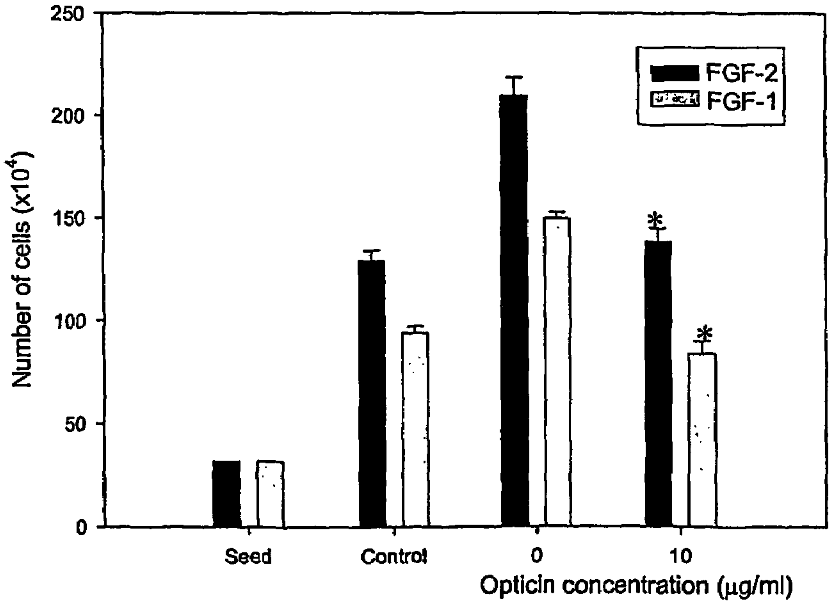

Figure 5 Proliferation assays with $VEGF_{164}$
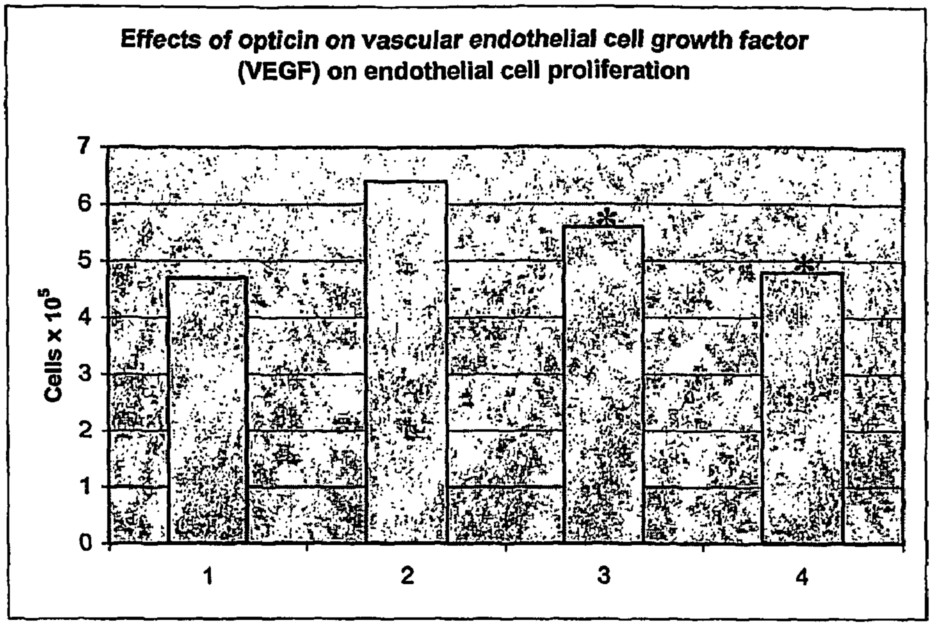
1 = Control
2 = $VEGF_{164}$ alone
3 = $VEGF_{164}$ + 1 μg/ml opticin
4 = $VEGF_{164}$ + 10 μg/ml opticin
* Denotes significant decrease in proliferation
Figure 6. Proliferation assays comparing $VEGF_{164}$ with $VEGF_{120}$
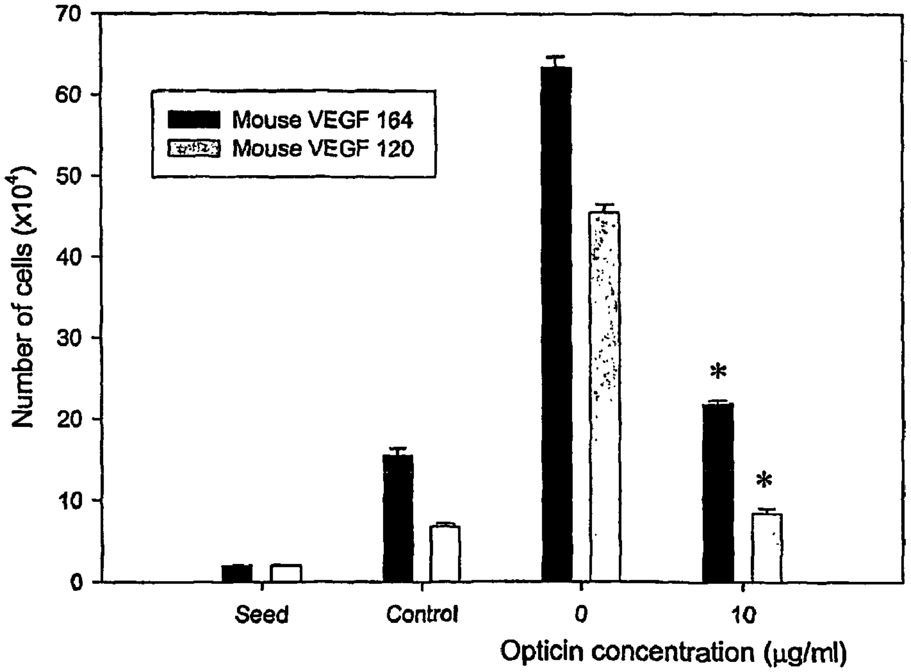

Figure 7. Exemplar images of sprout/tube formation assay with FGF-2
Control
With FGF-2
With FGF-2 and opticin 10 μg/ml
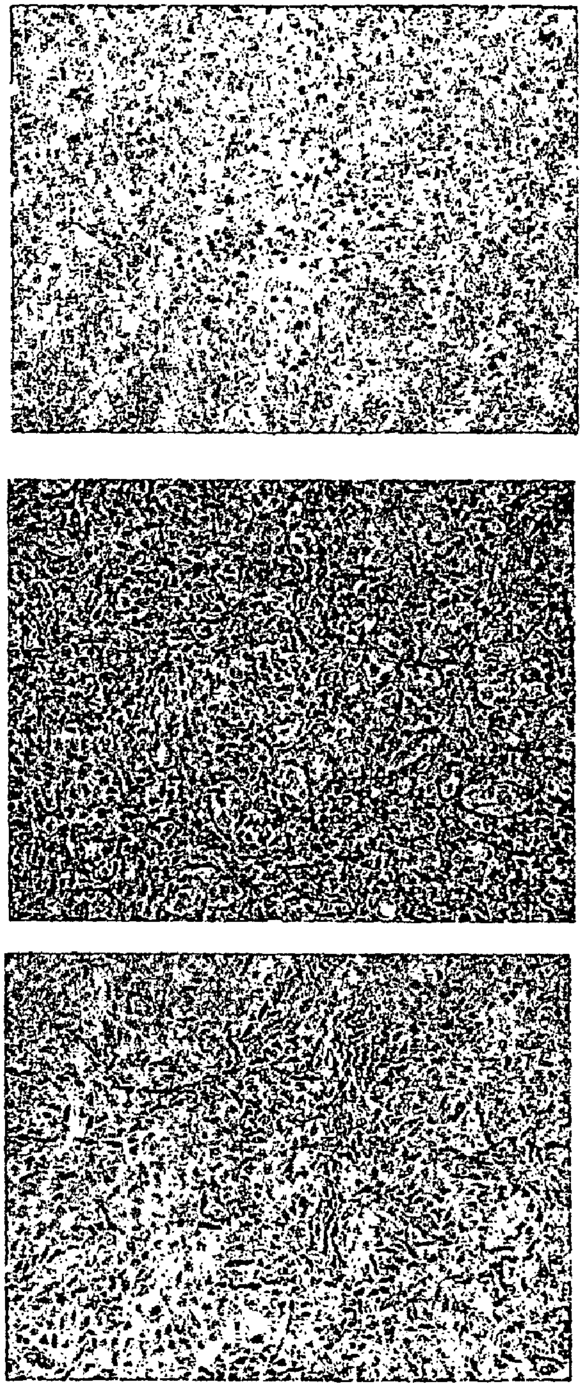

Figure 8. Graphical representation of data from tube/sprout formation assays with FGF-2 and $VEGF_{164}$
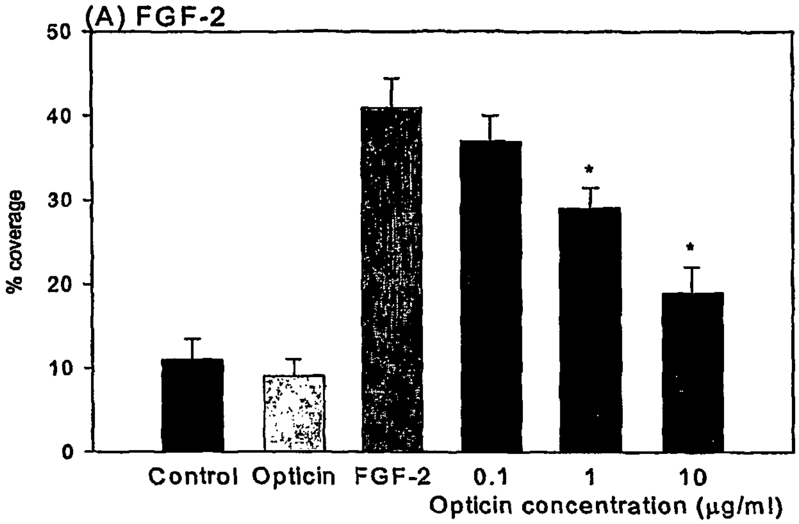
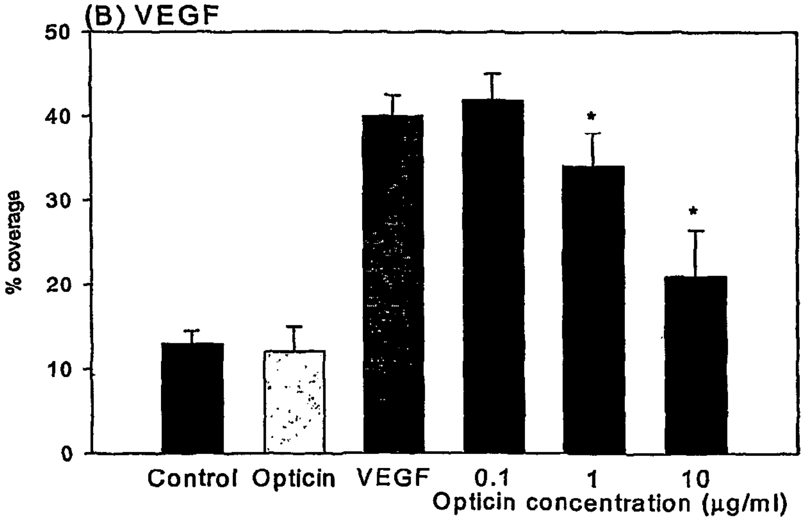

Figure 9. Vascular endothelial cell migration assay with $VEGF_{164}$ and FGF-2
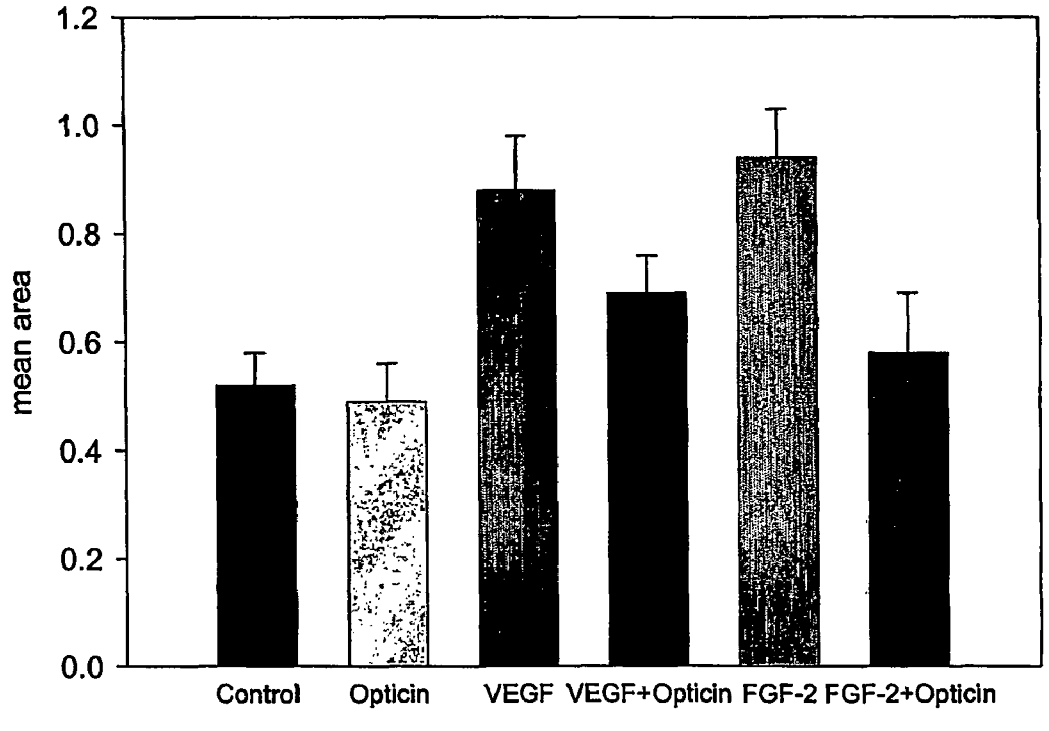

Figure 10. Decreased ERK-1/2 phosphorylation when cells stimutlated by $VEGF_{164}$ and FGF-2 in the presence of opticin
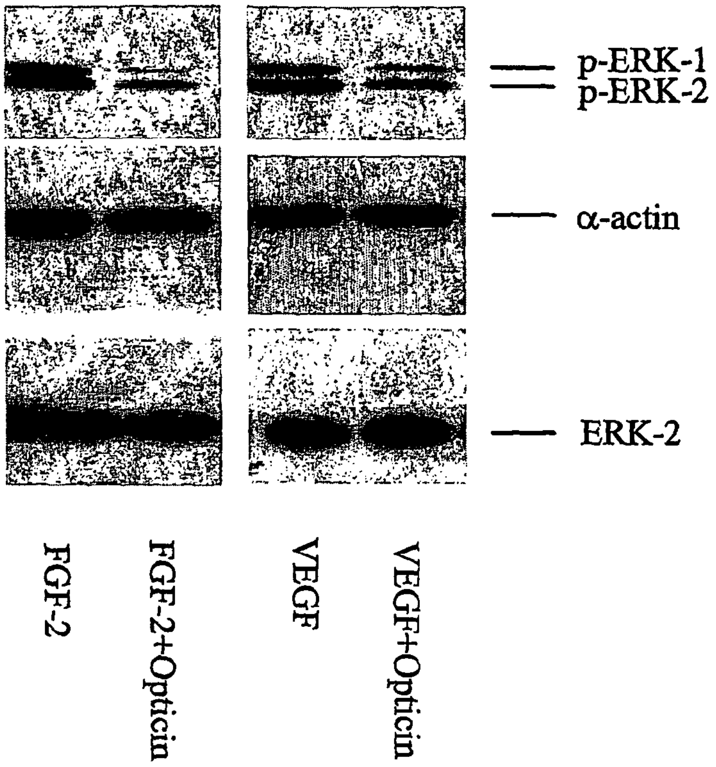

Figure 11. Chick chorioallantoic membrane (CAM) assay
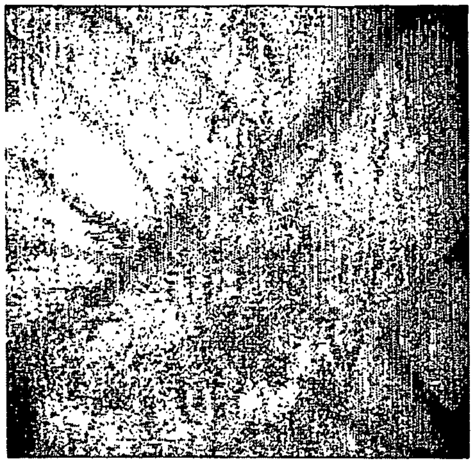
FGF-2
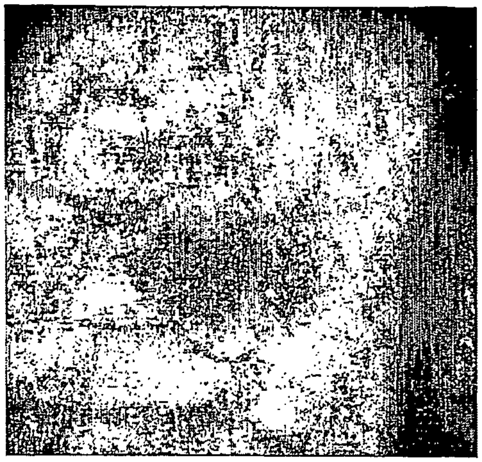
FGF-2 + opticin

Figure 12. Cell-spreading assays
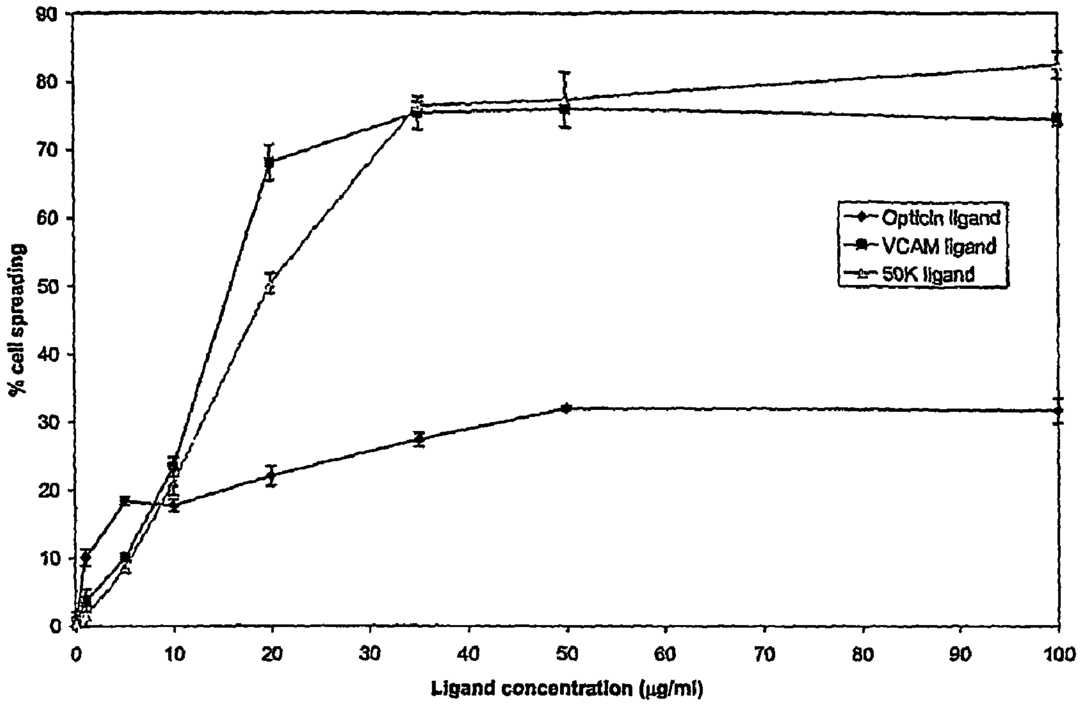

Figure 13. Cell-spreading assays with function blocking integrins
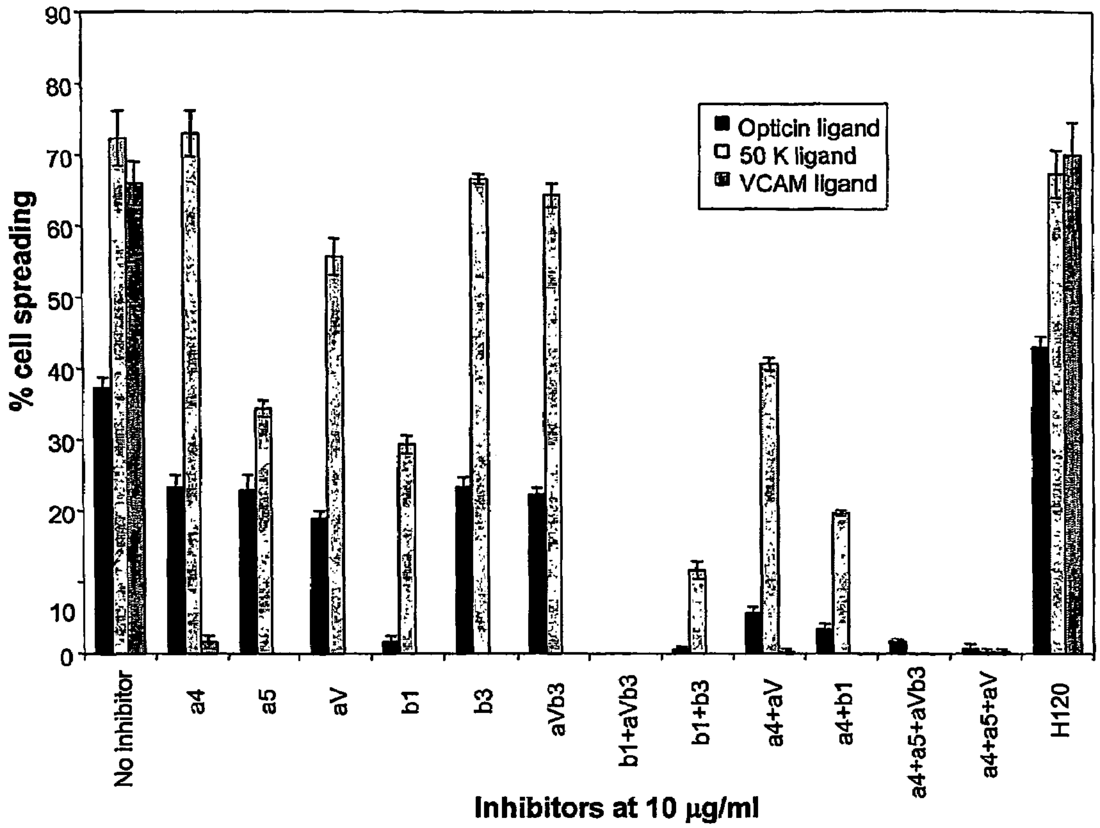

Figure 14. Solid-phase binding assays
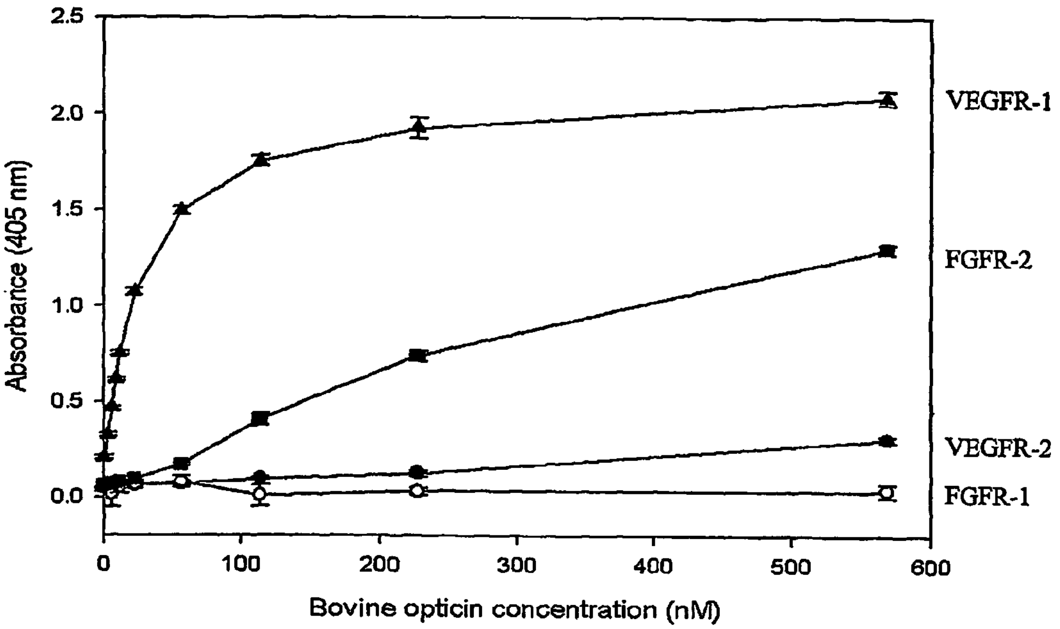
Figure 15. Graph showing solid-phase binding with opticin binding to $VEGF_{164}$ and FGF-2 but not $VEGF_{120}$ and FGF-1.
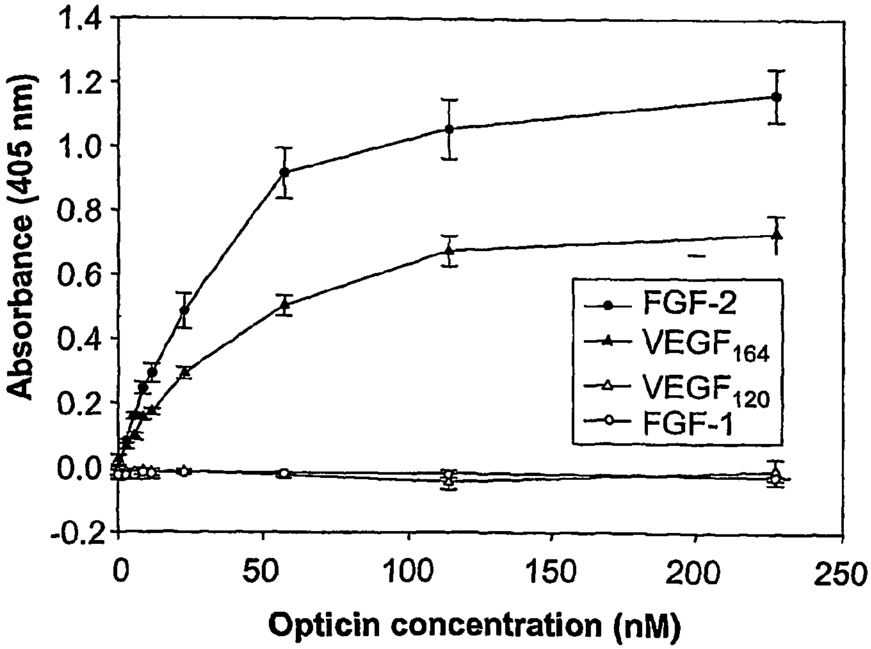

Figure 16. Solid-phase competition assays
(A) Opticin, by binding FGF-2 inhibits its interaction with the growth factor receptor FGFR-1
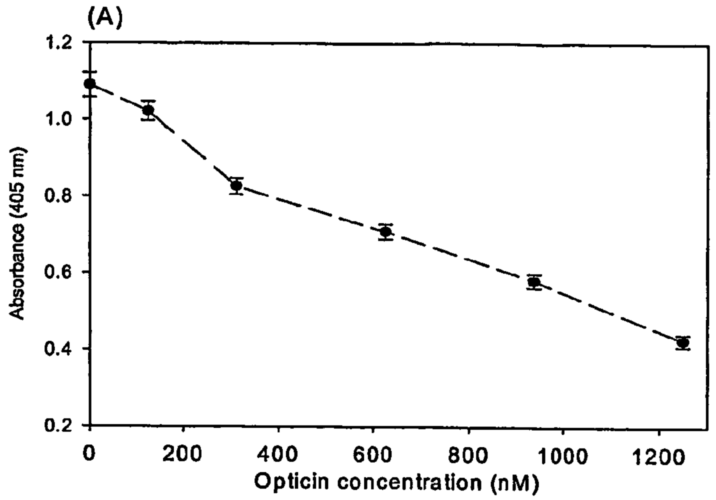
(B) Opticin, by binding $VEGF_{164}$ inhibits its interaction with the growth factor receptor VEGFR-2
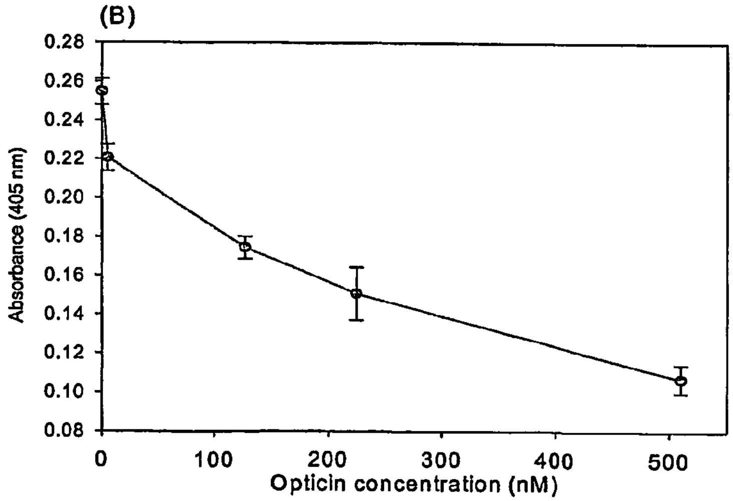

SEQUENCE LISTING

<160> NUMBER OF SEQ ID NOS: 14

<210> SEQ ID NO 1
<211> LENGTH: 313
<212> TYPE: PRT
<213> ORGANISM: Homo sapiens

<400> SEQUENCE: 1

```
Ala Ser Leu Pro Arg Lys Glu Arg Lys Arg Arg Glu Glu Gln Met Pro
1               5                   10                  15

Arg Glu Gly Asp Ser Phe Glu Val Leu Pro Leu Arg Asn Asp Val Leu
            20                  25                  30

Asn Pro Asp Asn Tyr Gly Glu Val Ile Asp Leu Ser Asn Tyr Glu Glu
        35                  40                  45

Leu Thr Asp Tyr Gly Asp Gln Leu Pro Glu Val Lys Val Thr Ser Leu
    50                  55                  60

Ala Pro Ala Thr Ser Ile Ser Pro Ala Lys Ser Thr Thr Ala Pro Gly
65                  70                  75                  80

Thr Pro Ser Ser Asn Pro Thr Met Thr Arg Pro Thr Thr Ala Gly Leu
                85                  90                  95

Leu Leu Ser Ser Gln Pro Asn His Gly Leu Pro Thr Cys Leu Val Cys
            100                 105                 110

Val Cys Leu Gly Ser Ser Val Tyr Cys Asp Asp Ile Asp Leu Glu Asp
        115                 120                 125

Ile Pro Pro Leu Pro Arg Arg Thr Ala Tyr Leu Tyr Ala Arg Phe Asn
    130                 135                 140

Arg Ile Ser Arg Ile Arg Ala Glu Asp Phe Lys Gly Leu Thr Lys Leu
145                 150                 155                 160

Lys Arg Ile Asp Leu Ser Asn Asn Leu Ile Ser Ser Ile Asp Asn Asp
                165                 170                 175

Ala Phe Arg Leu Leu His Ala Leu Gln Asp Leu Ile Leu Pro Glu Asn
            180                 185                 190

Gln Leu Glu Ala Leu Pro Val Leu Pro Ser Gly Ile Glu Phe Leu Asp
        195                 200                 205

Val Arg Leu Asn Arg Leu Gln Ser Ser Gly Ile Gln Pro Ala Ala Phe
    210                 215                 220

Arg Ala Met Glu Lys Leu Gln Phe Leu Tyr Leu Ser Asp Asn Leu Leu
225                 230                 235                 240

Asp Ser Ile Pro Gly Pro Leu Pro Leu Ser Leu Arg Ser Val His Leu
                245                 250                 255

Gln Asn Asn Leu Ile Glu Thr Met Gln Arg Asp Val Phe Cys Asp Pro
            260                 265                 270

Glu Glu His Lys His Thr Arg Arg Gln Leu Glu Asp Ile Arg Leu Asp
        275                 280                 285

Gly Asn Pro Ile Asn Leu Ser Leu Phe Pro Ser Ala Tyr Phe Cys Leu
    290                 295                 300

Pro Arg Leu Pro Ile Gly Arg Phe Thr
305                 310
```

<210> SEQ ID NO 2
<211> LENGTH: 302
<212> TYPE: PRT
<213> ORGANISM: Bos taurus

<400> SEQUENCE: 2

-continued

```
Ala Ser Leu Ser Glu Glu Arg Glu Gly Asp Pro Tyr Ala Ile Leu His
1               5                   10                  15

Leu Gly Asp Tyr Val Leu Ser Leu Asp Asn Tyr Asp Glu Val Ile Asp
            20                  25                  30

Pro Ser Asn Tyr Asp Glu Leu Ile Asp Tyr Gly Asp Gln Leu Pro Gln
        35                  40                  45

Val Lys Gly Thr Ser Leu Ala Ser Leu Thr Arg Thr Arg Phe Thr Gln
    50                  55                  60

Ser Thr Glu Ala Ala Arg Thr Leu Pro Ser Asn Pro Thr Thr Ala Arg
65                  70                  75                  80

Pro Pro Thr Leu Gly Leu Leu Ala Ala Pro Ala Asn His Gly Leu Pro
                85                  90                  95

Thr Cys Leu Ile Cys Val Cys Leu Gly Ser Ser Val Tyr Cys Asp Asp
            100                 105                 110

Ala Asp Leu Glu Asn Ile Pro Pro Leu Pro Gln Thr Thr Ala Tyr Leu
        115                 120                 125

Tyr Ala Arg Phe Asn Arg Ile Ser His Ile Arg Ala Gly Asp Phe Lys
    130                 135                 140

Gly Leu Thr Lys Leu Lys Arg Ile Asp Leu Ser Gly Asn Ser Ile Ser
145                 150                 155                 160

Ser Ile Asp Asp Lys Ala Leu Arg Leu Leu Pro Ala Leu Arg Asp Leu
                165                 170                 175

Ile Leu Pro Glu Asn Lys Leu Val Ala Leu Pro Thr Leu Pro Thr Ser
            180                 185                 190

Ile Glu Val Leu Asp Val Arg Met Asn Arg Leu Gln Ser Ser Gly Ile
        195                 200                 205

Gln Pro Glu Ala Phe Arg Ala Leu Glu Lys Leu Gln Phe Leu Tyr Leu
    210                 215                 220

Ala Asp Asn Leu Leu Asp Ala Ile Pro Pro Ser Leu Pro Leu Ser Leu
225                 230                 235                 240

Arg Ser Leu His Leu Gln Asn Asn Met Ile Glu Thr Met Gln Arg Asp
                245                 250                 255

Ala Phe Cys Asp Ala Glu Glu His Arg His Thr Arg Arg Pro Leu Glu
            260                 265                 270

Asp Ile Arg Leu Asp Gly Asn Pro Ile Asn Leu Ser Leu Phe Pro Ser
        275                 280                 285

Ala Tyr Phe Cys Leu Pro Arg Leu Pro Thr Gly Arg Phe Val
    290                 295                 300


<210> SEQ ID NO 3
<211> LENGTH: 300
<212> TYPE: PRT
<213> ORGANISM: Homo sapiens

<400> SEQUENCE: 3

Ala Pro Thr Leu Glu Ser Ile Asn Tyr Asp Ser Glu Thr Tyr Asp Ala
1               5                   10                  15

Thr Leu Glu Asp Leu Asp Asn Leu Tyr Asn Tyr Glu Asn Ile Pro Val
            20                  25                  30

Gly Lys Val Glu Ile Glu Ile Ala Thr Val Met Pro Ser Gly Asn Arg
        35                  40                  45

Glu Leu Leu Thr Pro Pro Pro Gln Pro Glu Lys Ala Gln Glu Glu Glu
    50                  55                  60

Glu Glu Glu Glu Ser Thr Pro Arg Leu Ile Asp Gly Ser Ser Pro Gln
```

-continued

```
65                  70                  75                  80

Glu Pro Glu Phe Thr Gly Val Leu Gly Pro His Thr Asn Glu Asp Phe
                85                  90                  95

Pro Thr Cys Leu Leu Cys Thr Cys Ile Ser Thr Thr Val Tyr Cys Asp
            100                 105                 110

Asp His Glu Leu Ala Ile Pro Pro Leu Pro Lys Asn Thr Ala Tyr Phe
        115                 120                 125

Tyr Ser Arg Phe Asn Arg Ile Lys Lys Ile Asn Lys Asn Asp Phe Ala
    130                 135                 140

Ser Leu Ser Asp Leu Lys Arg Ile Asp Leu Thr Ser Asn Leu Ile Ser
145                 150                 155                 160

Glu Ile Asp Glu Asp Ala Phe Arg Lys Leu Pro Gln Leu Arg Glu Leu
                165                 170                 175

Val Leu Arg Asp Asn Lys Ile Arg Gln Glu Leu Pro Thr Thr Leu Thr
            180                 185                 190

Phe Ile Asp Ile Ser Asn Asn Arg Leu Gly Arg Lys Gly Ile Lys Gln
        195                 200                 205

Glu Ala Phe Lys Asp Met Tyr Asp Leu His His Leu Tyr Leu Thr Asp
    210                 215                 220

Asn Asn Leu Asp His Ile Pro Leu Pro Leu Pro Glu Asn Leu Arg Ala
225                 230                 235                 240

Leu His Leu Gln Asn Asn Asn Ile Leu Glu Met His Glu Asp Thr Phe
                245                 250                 255

Cys Asn Val Lys Asn Leu Thr Tyr Ile Arg Lys Ala Leu Glu Asp Ile
            260                 265                 270

Arg Leu Asp Gly Asn Pro Ile Asn Leu Ser Lys Thr Pro Gln Ala Tyr
        275                 280                 285

Met Cys Leu Pro Arg Leu Pro Val Gly Ser Leu Val
    290                 295                 300


<210> SEQ ID NO 4
<211> LENGTH: 281
<212> TYPE: PRT
<213> ORGANISM: Homo sapiens

<400> SEQUENCE: 4

Lys Pro Ala Pro Pro Thr Gln Gln Asp Ser Arg Ile Ile Tyr Asp Tyr
1               5                   10                  15

Gly Thr Asp Asn Phe Glu Glu Ser Ile Phe Ser Gln Asp Tyr Glu Asp
            20                  25                  30

Lys Tyr Leu Asp Gly Lys Asn Ile Lys Glu Lys Glu Thr Val Ile Ile
        35                  40                  45

Pro Asn Glu Lys Ser Leu Gln Leu Gln Lys Asp Glu Ala Ile Thr Pro
    50                  55                  60

Leu Pro Pro Lys Lys Glu Asn Asp Glu Met Pro Thr Cys Leu Leu Cys
65                  70                  75                  80

Val Cys Leu Ser Gly Ser Val Tyr Cys Glu Glu Val Asp Ile Asp Ala
                85                  90                  95

Val Pro Pro Leu Pro Lys Glu Ser Ala Tyr Leu Tyr Ala Arg Phe Asn
            100                 105                 110

Lys Ile Lys Lys Leu Thr Ala Lys Asp Phe Ala Asp Ile Pro Asn Leu
        115                 120                 125

Arg Arg Leu Asp Phe Thr Gly Asn Leu Ile Glu Asp Ile Glu Asp Gly
    130                 135                 140
```

-continued

```
Thr Phe Ser Lys Leu Ser Leu Leu Glu Glu Leu Ser Leu Ala Glu Asn
145                 150                 155                 160

Gln Leu Leu Lys Leu Pro Val Leu Pro Pro Lys Leu Thr Leu Phe Asn
                165                 170                 175

Ala Lys Tyr Asn Lys Ile Lys Ser Arg Gly Ile Lys Ala Asn Ala Phe
            180                 185                 190

Lys Lys Leu Asn Asn Leu Thr Phe Leu Tyr Leu Asp His Asn Ala Leu
        195                 200                 205

Glu Ser Val Pro Leu Asn Leu Pro Glu Ser Leu Arg Val Ile His Leu
    210                 215                 220

Gln Phe Asn Asn Ile Ala Ser Ile Thr Asp Asp Thr Phe Cys Lys Ala
225                 230                 235                 240

Asn Asp Thr Ser Tyr Ile Arg Asp Arg Ile Glu Glu Ile Arg Leu Glu
                245                 250                 255

Gly Asn Pro Ile Val Leu Gly Lys His Pro Asn Ser Phe Ile Cys Leu
            260                 265                 270

Lys Arg Leu Pro Ile Gly Ser Tyr Phe
        275                 280


<210> SEQ ID NO 5
<211> LENGTH: 209
<212> TYPE: PRT
<213> ORGANISM: Homo sapiens

<400> SEQUENCE: 5

Gly Leu Pro Thr Cys Leu Val Cys Val Cys Leu Gly Ser Ser Val Tyr
1               5                   10                  15

Cys Asp Asp Ile Asp Leu Glu Asp Ile Pro Pro Leu Pro Arg Arg Thr
            20                  25                  30

Ala Tyr Leu Tyr Ala Arg Phe Asn Arg Ile Ser Arg Ile Arg Ala Glu
        35                  40                  45

Asp Phe Lys Gly Leu Thr Lys Leu Lys Arg Ile Asp Leu Ser Asn Asn
    50                  55                  60

Leu Ile Ser Ser Ile Asp Asn Asp Ala Phe Arg Leu Leu His Ala Leu
65                  70                  75                  80

Gln Asp Leu Ile Leu Pro Glu Asn Gln Leu Glu Ala Leu Pro Val Leu
                85                  90                  95

Pro Ser Gly Ile Glu Phe Leu Asp Val Arg Leu Asn Arg Leu Gln Ser
            100                 105                 110

Ser Gly Ile Gln Pro Ala Ala Phe Arg Ala Met Glu Lys Leu Gln Phe
        115                 120                 125

Leu Tyr Leu Ser Asp Asn Leu Leu Asp Ser Ile Pro Gly Pro Leu Pro
    130                 135                 140

Leu Ser Leu Arg Ser Val His Leu Gln Asn Asn Leu Ile Glu Thr Met
145                 150                 155                 160

Gln Arg Asp Val Phe Cys Asp Pro Glu Glu His Lys His Thr Arg Arg
                165                 170                 175

Gln Leu Glu Asp Ile Arg Leu Asp Gly Asn Pro Ile Asn Leu Ser Leu
            180                 185                 190

Phe Pro Ser Ala Tyr Phe Cys Leu Pro Arg Leu Pro Ile Gly Arg Phe
        195                 200                 205

Thr


<210> SEQ ID NO 6
<211> LENGTH: 209
```

-continued

```
<212> TYPE: PRT
<213> ORGANISM: Homo sapiens

<400> SEQUENCE: 6

Asp Phe Pro Thr Cys Leu Trp Cys Thr Cys Ile Ser Thr Thr Val Tyr
1               5                   10                  15

Cys Asp Asp His Glu Leu Asp Ala Ile Pro Pro Leu Pro Lys Asn Thr
            20                  25                  30

Ala Tyr Phe Tyr Ser Arg Phe Asn Arg Ile Lys Lys Ile Asn Lys Asn
        35                  40                  45

Asp Phe Ala Ser Leu Ser Asp Leu Lys Arg Ile Asp Leu Thr Ser Asn
    50                  55                  60

Leu Ile Ser Glu Ile Asp Glu Asp Ala Phe Arg Lys Leu Pro Gln Leu
65                  70                  75                  80

Arg Glu Leu Val Leu Arg Asp Asn Lys Ile Arg Gln Leu Pro Glu Leu
                85                  90                  95

Pro Thr Thr Ser Thr Phe Ile Asp Ile Ser Asn Asn Arg Leu Gly Arg
            100                 105                 110

Lys Gly Ile Lys Gln Glu Ala Phe Lys Asp Met Tyr Asp Leu His His
        115                 120                 125

Leu Tyr Leu Thr Asp Asn Asn Leu Asp His Ile Pro Leu Pro Leu Pro
    130                 135                 140

Glu Asn Leu Arg Ala Leu His Leu Gln Asn Asn Asn Ile Leu Glu Met
145                 150                 155                 160

His Glu Asp Thr Phe Cys Asn Gly Lys Asn Leu Thr Tyr Ile Arg Lys
                165                 170                 175

Ala Leu Glu Asp Ile Arg Leu Asp Gly Asn Pro Ile Asn Leu Ser Lys
            180                 185                 190

Thr Pro Gln Ala Tyr Met Cys Leu Pro Arg Leu Pro Val Gly Ser Leu
        195                 200                 205

Val


<210> SEQ ID NO 7
<211> LENGTH: 209
<212> TYPE: PRT
<213> ORGANISM: Homo sapiens

<400> SEQUENCE: 7

Glu Met Pro Thr Cys Leu Leu Cys Val Cys Leu Ser Gly Ser Val Tyr
1               5                   10                  15

Cys Glu Glu Val Asp Ile Asp Ala Val Pro Pro Leu Pro Lys Glu Ser
            20                  25                  30

Ala Tyr Leu Tyr Ala Arg Phe Asn Lys Ile Lys Lys Leu Thr Ala Lys
        35                  40                  45

Asp Phe Ala Asp Ile Pro Asn Leu Arg Arg Leu Asp Phe Thr Gly Asn
    50                  55                  60

Leu Ile Glu Asp Ile Glu Asp Gly Thr Phe Ser Lys Leu Ser Leu Leu
65                  70                  75                  80

Glu Glu Leu Ser Leu Ala Glu Asn Gln Leu Leu Lys Leu Pro Val Leu
                85                  90                  95

Pro Pro Lys Leu Thr Leu Phe Asn Ala Lys Tyr Asn Lys Ile Lys Ser
            100                 105                 110

Arg Gly Ile Lys Ala Asn Ala Phe Lys Lys Leu Asn Asn Leu Thr Phe
        115                 120                 125

Leu Tyr Leu Asp His Asn Ala Leu Glu Ser Val Pro Leu Asn Leu Pro
```

-continued

```
    130                 135                 140

Glu Ser Leu Arg Val Ile His Leu Gln Phe Asn Asn Ile Ala Ser Ile
145                 150                 155                 160

Thr Asp Asp Thr Phe Cys Lys Ala Asn Asp Thr Ser Tyr Ile Arg Asp
                165                 170                 175

Arg Ile Glu Glu Ile Arg Leu Glu Gly Asn Pro Ile Val Leu Gly Lys
            180                 185                 190

His Pro Asn Ser Phe Ile Cys Leu Lys Arg Leu Pro Ile Gly Ser Tyr
        195                 200                 205

Phe


<210> SEQ ID NO 8
<211> LENGTH: 87
<212> TYPE: PRT
<213> ORGANISM: Bos taurus

<400> SEQUENCE: 8

Ala Ser Leu Ser Glu Glu Arg Glu Gly Asp Pro Tyr Ala Ile Leu His
1               5                   10                  15

Leu Gly Asp Tyr Val Leu Ser Leu Asp Asn Tyr Asp Glu Val Ile Asp
            20                  25                  30

Pro Ser Asn Tyr Asp Glu Leu Ile Asp Tyr Gly Asp Gln Leu Pro Gln
        35                  40                  45

Val Lys Gly Thr Ser Leu Ala Ser Leu Thr Arg Thr Arg Phe Thr Gln
    50                  55                  60

Ser Thr Glu Ala Ala Arg Thr Leu Pro Ser Asn Pro Thr Thr Ala Arg
65                  70                  75                  80

Pro Pro Thr Leu Gly Leu Leu
                85


<210> SEQ ID NO 9
<211> LENGTH: 24
<212> TYPE: PRT
<213> ORGANISM: Homo sapiens

<400> SEQUENCE: 9

Asp Asn Tyr Gly Glu Val Ile Asp Leu Ser Asn Tyr Glu Glu Leu Thr
1               5                   10                  15

Asp Tyr Gly Asp Gln Leu Pro Glu
            20


<210> SEQ ID NO 10
<211> LENGTH: 24
<212> TYPE: PRT
<213> ORGANISM: Bos taurus

<400> SEQUENCE: 10

Asp Asn Tyr Asp Glu Val Ile Asp Pro Ser Asn Tyr Asp Glu Leu Ile
1               5                   10                  15

Asp Tyr Gly Asp Gln Leu Pro Gln
            20


<210> SEQ ID NO 11
<211> LENGTH: 90
<212> TYPE: PRT
<213> ORGANISM: Bos taurus

<400> SEQUENCE: 11

Ala Ser Leu Ser Glu Glu Arg Glu Gly Asp Pro Tyr Ala Ile Leu His
```

-continued

```
1               5                   10                  15

Leu Gly Asp Tyr Val Leu Ser Leu Asp Asn Tyr Asp Glu Val Ile Asp
            20                  25                  30

Pro Ser Asn Tyr Asp Glu Leu Ile Asp Tyr Gly Asp Gln Leu Pro Gln
        35                  40                  45

Val Lys Gly Thr Ser Leu Ala Ser Leu Thr Arg Thr Arg Phe Thr Gln
    50                  55                  60

Ser Thr Glu Ala Ala Arg Thr Leu Pro Ser Asn Pro Thr Thr Ala Arg
65                  70                  75                  80

Pro Pro Thr Leu Gly Leu Leu Ala Ala Pro
                85                  90


<210> SEQ ID NO 12
<211> LENGTH: 96
<212> TYPE: PRT
<213> ORGANISM: Canis familiaris

<400> SEQUENCE: 12

Ala Ser Leu Pro Lys Glu Arg Lys Arg Arg Asp Glu Met His Gly Glu
1               5                   10                  15

Gly Asp Ser Tyr Val Val Leu Gly Asn Tyr Val Leu Gly Pro Asp Asn
            20                  25                  30

Tyr Asp Glu Val Ile Asp Leu Ser Asp Tyr Glu Gly Leu Met Asp Tyr
        35                  40                  45

Gly Asp Gln Leu Pro Glu Ala Lys Val Thr Asn Leu Ala Pro Pro Thr
    50                  55                  60

Gly Ile Ser Ser Ala Gln Ser Thr Met Thr Pro Arg Thr Leu Ser Leu
65                  70                  75                  80

Lys Pro Thr Met Ile Arg Pro Thr Glu Leu Gly Val Leu Gly Ser Pro
                85                  90                  95


<210> SEQ ID NO 13
<211> LENGTH: 100
<212> TYPE: PRT
<213> ORGANISM: Homo sapiens

<400> SEQUENCE: 13

Ala Ser Leu Pro Arg Lys Glu Arg Lys Arg Arg Glu Glu Gln Met Pro
1               5                   10                  15

Arg Glu Gly Asp Ser Phe Glu Val Leu Pro Leu Arg Asn Asp Val Leu
            20                  25                  30

Asn Pro Asp Asn Tyr Gly Glu Val Ile Asp Leu Ser Asn Tyr Glu Glu
        35                  40                  45

Leu Thr Asp Tyr Gly Asp Gln Leu Pro Glu Val Lys Val Thr Ser Leu
    50                  55                  60

Ala Pro Ala Thr Ser Ile Ser Pro Ala Lys Ser Thr Thr Ala Pro Gly
65                  70                  75                  80

Thr Thr Ser Ser Asn Pro Thr Met Thr Arg Pro Thr Thr Ala Gly Leu
                85                  90                  95

Leu Leu Ser Ser
            100


<210> SEQ ID NO 14
<211> LENGTH: 97
<212> TYPE: PRT
<213> ORGANISM: Mus musculus

<400> SEQUENCE: 14
```

-continued

```
Ala Ser Leu Leu Gly Glu Arg Glu Arg Glu Glu Gln Ser Pro Glu Glu
1               5                   10                  15

Gly Asp Thr Tyr Ala Ser Leu Tyr Val Gly Asn His Thr Leu Ser Ile
            20                  25                  30

Glu Asp Tyr Asn Glu Val Ile Asp Leu Ser Asn Tyr Glu Glu Leu Ala
        35                  40                  45

Asp Tyr Gly Asp Gln Ile Pro Glu Ala Lys Ile Ser Asn Leu Thr Leu
    50                  55                  60

Pro Thr Arg Thr Ser Pro Thr Ser Thr Val Ala Gln Lys Thr Leu Ser
65                  70                  75                  80

Pro Asn Leu Thr Met Ala Val Pro Thr Thr Thr Gly Leu Leu Asn Ser
                85                  90                  95

Gln
```

CLASS III SLRP AGONISTS FOR THE REDUCTION OF BLOOD VESSEL FORMATION

CROSS-REFERENCE TO RELATED APPLICATIONS

This patent application is a national stage filing under 35 U.S.C. 371 of International Application No. PCT/GB2004/002269, filed May 28, 2004, which claims foreign priority benefits to Great Britain No. 0312292.6, filed May 29, 2003 and Great Britain No. 0400547.6, filed Jan. 12, 2004.

The present invention relates to medicaments for the reduction of new blood vessel formation, and for the treatment and/or prevention of a condition characterised by excessive blood vessel formation. It further provides medicaments for the prevention and/or treatment of conditions characterised by excessive activity and/or migration of monocytes and/or macrophages.

The formation of new blood vessels arises primarily as result of angiogenesis (a sprouting outgrowth from existing blood vessels) and in situ vasculogenesis (the differentiation of precursor cells into blood vessel networks). In many contexts new blood vessel formation plays an important role in the supply of oxygen and nutrients to developing or damaged tissues, however there are also many pathological conditions associated with new blood vessel formation.

Examples of diseases associated with new blood vessel formation include cancer, where the development of new blood vessels is associated with tumour growth and propagation, the vasoproliferative retinopathies including proliferative diabetic retinopathy, retinopathy of prematurity and sickle cell retinopathy, ‘wet’ macular degeneration and other forms of choroidal neovascularisation, psoriasis, and many inflammatory conditions such as arthritis.

Vasoproliferative retinopathies, in which the eye is subject to pathologically increased vascularisation, constitute one of the leading causes of visual impairment and blindness in the western world. Proliferative diabetic retinopathy is characterised by vitreous haemorrhage, retinal detachment, neovascular glaucoma and consequent visual loss.

The excessive activity and/or migration of monocytes and/or macrophages is part of the process of pathological angiogenesis and, in addition, is associated with many inflammatory conditions. Examples of such conditions include septic shock, glomerulonephritis, inflammatory bowel disease and rheumatoid arthritis. The excessive activity and/or migration of cells of the monocyte/macrophage lineage is responsible for many of the deleterious effects associated with such conditions. For example, in rheumatoid arthritis the activity of macrophages makes a major contributor to the destruction of joint tissue and bone associated with the disease.

Due to the number of contexts in which new blood vessel formation may be considered undesirable there remains a need for new agents capable of inhibiting blood vessel formation.

The invention will be further described in the following Examples, with reference to the accompanying drawings in which:

FIG. 1 represents the full-length amino acid sequences of mature human and bovine opticin, human epiphycan and human mimecan, as well as illustrating amino acid alignment between the leucine-rich repeat regions of the human class III SLRPs;

FIGS. 2*a*, 2*b*, and 2 illustrates in Panel 2*a* the amino acid sequence of an NH terminal fragment of bovine opticin that is released on digestion with the metalloproteinases MMP2 or MMP9, in Panel 2*b* the amino acid sequence of preferred fragments of human and bovine opticin, and in Panel 2*c* amino acid alignment between the NH terminal opticin sequences from different species FIG. 3 is a graph illustrating that the class III SLRP opticin inhibits vascular endothelial cell proliferation induced by basic fibroblast growth factor (FGF-2) in Example 1;

FIG. 4 graphically illustrates the effect of opticin on endothelial cell proliferation induced by acidic or basic FGF;

FIG. 5 is a graph illustrating that the class III SLRP opticin inhibits vascular endothelial cell proliferation induced by vascular endothelial growth factor (VEGF) in Example 1;

FIG. 6 graphically illustrates the effect of opticin on endothelial cell proliferation induced by $VEGF_{164}$ or $VEGF_{120}$;

FIG. 7 shows representative photographs illustrating that the class III SLRP opticin inhibits BAEC sprout/tube formation induced by FGF-2 in Example 2;

FIG. 8 shows the results of experiments investigating the ability of the class III SLRP opticin to inhibit vascular endothelial cell sprout/tube formation in Example 2;

FIG. 9 shows the results of experiments investigating the ability of the class III SLRP opticin to inhibit endothelial cell migration in Example 3

FIG. 10 illustrates that the presence of the class III SLRP opticin reduces ERK-1/2 phosphorylation in $VEGF_{164}$ or FGF-2 stimulated cells in Example 4;

FIG. 11 illustrates that the class III SLRP opticin is able to inhibit FGF-2-induced blood vessel formation in a chick chorioallantoic membrane (CAM) assay of Example 5;

FIG. 12 shows the effects of the class III SLRP opticin on cell spreading in Example 6;

FIG. 13 shows the effects of the class III SLRP opticin and function-blocking integrin antibodies on cell spreading in Example 6;

FIG. 14 illustrates binding of the class III SLRP opticin to angiogenic growth factors receptors;

FIG. 15 illustrates binding of the class III SLRP opticin to angiogenic growth factors; and FIG. 16 illustrates that the class III SLRP opticin is able to prevent binding of angiogenic growth factors to their receptors in Example 7.

There also remains a need for agents able to prevent and/or treat conditions associated with excess activity and/or migration of monocytes and/or macrophages.

According to a first aspect of the present invention there is provided the use of an agent that promotes class III small leucine-rich repeat protein/proteoglycan (class III SLRP) activity in the manufacture of a medicament for the inhibition of blood vessel formation.

According to a second aspect of the invention there is provided the use of an agent that promotes class III small leucine-rich repeat protein/proteoglycan (class III SLRP) activity in the manufacture of a medicament for the prevention and/or treatment of conditions characterised by excessive activity and/or migration of monocytes and/or macrophages.

The term “agent that promotes class III SLRP activity” as used in the present application encompasses class III SLRPs per se; biologically active fragments of class III SLRPs; derivatives of class III SLRPs; and also agents that mimic class III SLRP activity.

References to "monocytes and/or macrophages" should be taken, except where the context dictates otherwise to encompass all cell types derived from the monocyte/macrophage cell lineage. In particular, this term should be considered to encompass hyalocytes.

The inventor has discovered that members of the class III small leucine-rich repeat protein/proteoglycan (SLRP) family, such as opticin (a class III SLRP that was first identified associated with collagen fibrils in the vitreous humour, and which is also known as oculoglycan), epiphycan, mimecan (which is also known as osteoglycin) are able to inhibit new blood vessel formation.

The invention will be further described in the following Examples, with reference to the accompanying drawings in which:

The amino acid sequences of opticin (both human and bovine forms), epiphycan and mimecan are shown in FIG. 1. This Figure also shows alignment of the amino acid sequences, illustrating the high degree of similarity between different members of the class III SLRP family.

FIGS. 2*a*, 2*b*, and 2 illustrates (in panel 2*a*) a biologically active fragment released on cleavage of the class III SLRP opticin with matrix metalloproteinases 2 or 9 (MMP-2 or MMP-9). Panel 2*b* shows peptide sequences from within the NH terminal region of human and bovine opticin that are preferred for their anti-angiogenic activity and ability to affect moncyte/macrophage These sequences are highly conserved between species, this great degree of conservation being indicative of their biological function. Panel 2*c* of FIG. 2 illustrates alignment of amino acid residues in the NH terminal region of opticin derived from different species (cow, dog, human and mouse).

In addition to their effects on new blood vessel formation, the inventors have also found that class III SLRPs will inhibit the activity and migration of monocytes and macrophages. The work conducted to establish both these findings is described in more detail in the Examples and accompanying Figures.

Class III SLRPs, modified forms of class III SLRPs, and biologically active fragments thereof, are able to inhibit new blood vessel formation in vitro and in vivo. Although we do not wish to be bound by any hypothesis the inventors believe that class III SLRPs inhibit the proliferation and re-arrangement of cultured vascular endothelial cells in response to angiogenic growth factors such as acidic fibroblast growth factor (aFGF or FGF-1) basic fibroblast growth factor (bFGF or FGF-2) and vascular endothelial cell growth factor (VEGF). These factors are amongst the best-known and most potent growth factors capable of stimulating new blood vessel formation.

The inventors have shown that class III SLRPs are able to bind to growth factors such as $VEGF_{165}$ and FGF-2, and believe that this binding may sequester the bound growth factor, thereby preventing the interaction of the bound growth factor with its corresponding receptors (such as VEGF-R2 and FGF-R1). Furthermore, the inventors have shown that class III SLRPs, such as opticin, are able to bind to the growth factor receptors themselves, and it is believed that this binding, and the consequent reduction in intracellular signalling from the receptors, may further contribute to the anti-angiogenic effects of the molecules.

VEGF-R1 and FGF-R2 are important receptors in angiogenesis and, in addition, mediate other important biological activities. In particular, VEGF-R1 is known to regulate cell migration of monocytes and macrophages. The inventors believe that this binding of class III SLRPs to VEGF-R1 may be responsible for the ability of these agents to inhibit monocyte/macrophage activity and/or migration and so to represent agents suitable for use in accordance with the second aspect of the invention.

In the light of the results discussed in the preceding paragraphs, the skilled person will appreciate that agents to be used in accordance with the present invention may be selected for their ability to bind to angiogenic growth factors or their receptors, and the ability to inhibit intracellular signalling by angiogenic growth factor receptors.

The inventors further believe that class III SLRPs are also able to inhibit new blood vessel formation by their interaction with integrins such as $\alpha4\beta1$, $\alpha v\beta3$ and $\alpha5\beta1$. This interaction inhibits endothelial adhesion, thereby preventing cell spreading and migration necessary for new blood vessel formation. For example, the inventors have found that the class III SLRP opticin contains an LDV (leucine-aspartic acid-valine) motif, which represents a potential recognition site for the $\alpha4\beta1$ integrin.

The inventors have found that class III SLRPs are able to inhibit angiogenesis in cultured vascular endothelial cells derived from diverse tissues. Class III SLRPs reduce endothelial cell proliferation, migration and sprout formation, and reduce new blood vessel formation as indicated in a chick chorioallantoic membrane (CAM) assay. Taken as a whole these results, which represent clear evidence of class III SLRPs' anti-neovascularisation properties in vitro, provide a clear indication that agents according to the invention are able to inhibit blood vessel formation in a range of tissues in vivo.

In addition to preventing new blood vessel formation associated with diseases and other damaging conditions, there are certain contexts in which it may be advantageous to inhibit new blood vessel formation associated with normal biological functions. Such a reduction in new blood vessel formation may, for instance, serve to reduce the availability of oxygen and blood-borne nutrients and growth factors to cells associated with a particular normal biological process, thereby slowing down the rate of the process in question.

It will be appreciated that the agents may be used in the prevention and/or treatment of conditions characterised by excessive blood vessel formation, as well as in the prevention and/or treatment of conditions characterised by excessive activity and/or migration of monocytes and/or macrophages.

Examples of conditions characterised by excessive blood vessel formation include cancer (where new blood vessel formation is associated with tumour growth), vasoproliferative retinopathies including proliferative diabetic retinopathy, 'wet' macular degeneration and other forms of choroidal neovascularisation, persistent primary hyperplastic vitreous (PPHV), psoriasis and wound healing. Other conditions involving pathological development of new blood vessels in the eye include subretinal neovascularisation, iris neovascularisation (which may lead to glaucoma), rubeosis, corneal neovascularisation and retinal neovascularisation.

Vasoproliferative retinopathies (VPRs) develop due to retinal microvascular closure and non-perfusion that results in retinal hypoxia and ischaemia. This hypoxia and ischaemia is believed to induce the production of angiogenic growth factors that cause preretinal neovasularisation and fibrosis, and consequently leads to the development of the pathological features of VPRs (which include vitreous haemorrhage, retinal detachment, neovascular glaucoma and resultant visual loss).

Conditions characterised by the excessive activity and/or migration of monocytes and/or macrophages include a wide range of inflammatory conditions (e.g. uveitis and arthritis). Many of these inflammatory conditions, such as arthritis, are also characterised by excessive blood vessel formation, making them particularly suitable for treatment with medicaments manufactured according to the first or second aspects of the invention. It is also known that pathological angiogenesis is associated with monocyte/macrophage activity, since these cells both stimulate the new blood vessel formation and act as markers for sites of future neovascularisation.

Agents used according to the first or second aspects of the invention may be any compound or composition that mimics the effect of class III SLRPs in vivo. However, it is preferred that the agent is:

a) opticin (also known as oculoglycan); or
b) epiphycan; or
c) mimecan (also known as osteoglycin); or
d) a chimeric molecule comprising elements of any of a) to c);
e) a modified form of any of a) to d); or
f) a biologically active fragment or derivative of any of a) to e).

It will be appreciated that agents suitable for use according to the invention encompass molecules able to mimic the activity of class III SLRPs. Such molecules may be capable of replicating the binding activity of class III SLRPs (e.g. capable of replicating binding to growth factors and/or their receptors). Preferred molecules may, for example, replicate the conformation of portions of class III SLRPs that are important in achieving their biological functions. Suitable agents capable of mimicking class III SLRP activity may include small soluble molecules.

It will further be appreciated that the binding properties of synthetic or natural agents suitable for use according to the invention may be modified, in accordance with the use to which the agent is to be put, to produce improved agents. For instance, agents to be used in accordance with the first aspect of the invention may be modified in order to increase their ability to bind angiogenic growth factors such as VEGF and FGF-2. Similarly, agents for use in accordance with the second aspect of the invention may be modified to increase their ability to bind receptors such as VEGF-R1.

The agent is preferably a human class III SLRP, or a fragment or derivative thereof. Most preferably the agent is human opticin or a fragment or derivative thereof.

In the event that the agent is a non-human class III SLRP, or a fragment or derivative thereof, it is preferred that the agent be one that is well tolerated in a human patient to which the agent is administered. A suitable non-human derived agent may be selected such that it contains few epitopes likely to contribute to the agent's rejection by a human patient, or may be "humanised" for example by modification to include portions of the corresponding human class III SLRP sequence. A preferred example of such an agent derived from a non-human class III SLRP is one derived from a bovine class III SLRP, such as bovine opticin.

Class III SLRPs may be isolated from naturally occurring sources. By way of example, the class III SLRP opticin is abundant in the vitreous humour of the eye, and accordingly may be enriched and isolated from this tissue. Alternatively class III SLRPs and their derivatives may be produced using recombinant DNA technologies. Preferably the agent may be a recombinant class III SLRP or a fragment or derivative thereof. Recombinant class III SLRPs and their derivatives maybe produced from many alternate sources, for instance bovine recombinant class III SLRPs such as opticin. More preferably such agents comprise a recombinant human class III SLRP or fragment or derivative thereof. Most preferably the agent is recombinant human opticin, or a fragment or derivative thereof.

The term "biologically active fragment of a class III SLRP" as used according to the invention encompasses fragments, which are able to replicate SLRPs' activities (both in terms of their ability to inhibit blood vessel formation, and their ability to prevent and/or reduce the migration and/or activity of monocytes or macrophages) as assessed by either in vivo or in vitro assays.

It is known that the class III SLRP opticin comprises a homodimer formed by non-covalently linked leucine-rich repeats (LRRs) linked to an amino-terminal (NH) domain. The LRR domain and NH domain may be enzymatically cleaved from one another, and such enzymatically cleaved class III SLRP fragments represent a preferred agent for use in accordance with the first and second aspects of the invention. Preferably enzymatic cleavage of class III SLRPs such as opticin may be undertaken using the matrix metalloproteinases MMP-2 or MMP-9. By way of example, the amino acid sequence of a NH terminal fragment derived by MMP-2 or MMP-9 cleavage of bovine opticin is illustrated in FIG. 2. The skilled person will appreciate that similar cleavage products may be produced on enzyme treatment of human class III SLRPs.

The NH domain fragment of enzymatically cleaved class III SLRPs are soluble and represent preferred agents suitable for use according to the invention. The NH domain may preferably be the NH domain of opticin.

Alternatively N-terminal fragments of class III SLRPs that have been derived by means other than enzymatic digestion may also be used as agents in accordance with the invention. By N-terminal fragment is meant any fragment comprising at least seven contiguous amino acids, preferably at least twelve contiguous amino acid residues, and more preferably at least twenty-four contiguous amino acid residues, from within the sixty-five amino acids located the N-terminal of a class III SLRP.

A preferred N-terminal fragment suitable for use in accordance with the invention may comprise one of the following amino acid sequences taken from the human and bovine forms of opticin:

```
                                              (SEQ ID NO: 9)
From human opticin: DNYGEVIDLSNYEELTDYGDQLPE

                                             (SEQ ID NO: 10)
From bovine opticin: DNYDEVIDPSNYDELIDYGDQLPQ
```

The above sequences are highly conserved between species, indicative of the importance of these amino acid residues in mediating class III SLRPs' biological activities.

Fragments of class III SLRPs other than those derived by enzyme cleavage may, for example, be produced by any suitable peptide synthesis methodology known in the art. The constituent amino acids of such synthesised fragments may be selected to include preferred portions of the class III SLRP sequence. The skilled person will appreciate that the range of possible non-enzymatically derived fragments of class III SLRPs is greater than that which may be derived by enzyme digest, since the potential sequences of such synthesised fragments are not constrained by the location of enzyme cleavage sites within the class III SLRP.

It will be appreciated that LRR regions of class III SLRPs may also represent suitable agents for use in accordance with the invention. The LRR region may suitably be utilised in the form of fragments including the LRR region of class III SLRPs. Such fragments may additionally comprise further amino acid residues from the C-terminal portion of a suitable class III SLRP. Fragments may be derived enzymatically or by other means, in the same way as considered above.

Preferably the LRR domain is the LRR of opticin, however the LRR domains of epiphycan and mimecan also represent suitable agents for use in accordance with the first and second aspects of the invention, since these LRR domains are also known to be glycosylated and to have relatively high solubility. LRR regions of the different class III SLRPs share a high degree of similarity with one another, as illustrated by the sequence alignment data shown in FIG. 1, and thus the skilled person would recognise that the biological activities associated with the LRR region of a particular class III SLRP may be expected to be common to other members of the family.

The ability of agents according to the invention to inhibit blood vessel formation may be readily tested in models well know to those skilled in the art. Examples of such assays include the chick chorioallantoic membrane model and cultured endothelial cell models (in which angiogenesis and/or vasculogenesis may be indicated by endothelial cell proliferation, migration and/or the formation of vascular endothelial cell "tubules" resembling blood vessels).

The ability of agents according to the invention to inhibit monocyte and/or macrophage activity and/or migration may also be assessed using assays well known to those skilled in the art. Examples of suitable assays for investigating this activity include Boyden chamber assays and the like.

Derivatives of class III SLRPs, or fragments thereof, may include derivatives of class III SLRPs that increase or decrease class III SLRPs' half-lives in vivo. Examples of derivatives that increase the half-life of class III SLRPs, or class III SLRP fragments, include modified class III SLRPs in which enzyme cleavage motifs have been removed by amino acid deletion and/or substitution, peptoid derivatives of class III SLRPs, D-amino acid derivatives of class III SLRPs and peptide-peptoid hybrids.

Agents such as native class III SLRPs, modified class III SLRPs or class III SLRP fragments, may be subject to degradation by a number of means (such as protease activity in biological systems). Such degradation may limit the bioavailability of class III SLRPs (or their fragments), and hence the ability of class III SLRPs to inhibit new blood vessel formation or to prevent monocyte/macrophage activity and/or migration. There are many examples of well-established techniques by which peptide derivatives that have enhanced stability in biological contexts can be designed and produced. Such peptide derivatives may have improved bioavailability as a result of increased resistance to protease-mediated degradation.

Preferably a peptide derivative or analogue suitable for use according to the invention is more protease-resistant than the peptide (or glycoprotein) from which it is derived. Suitable methods by which protease-resistance may be conferred include protection, substitution or modification of serine or threonine residues present in class III SLRPs. Protease-resistance of a peptide derivative and the peptide (or glycoprotein) from which it is derived may be evaluated by means of well-known protein degradation assays. The relative values of protease resistance for the peptide derivative and peptide (or glycoprotein or proteoglycan) may then be compared.

Peptoid derivatives of the agents of the invention may be readily designed from knowledge of the structure of class III SLRPs. Commercially available software may be used to develop peptoid derivatives according to well-established protocols.

Retropeptoids, (in which all amino acids are replaced by peptoid residues in reversed order) are also able to mimic a high-affinity binding proteins. A retropeptoid is expected to bind in the opposite direction in the ligand-binding groove, as compared to a peptide or peptoid-peptide hybrid containing one peptoid residue. As a result, the side chains of the peptoid residues are able point in the same direction as the side chains in the original peptide.

A further embodiment of a modified form of class III SLRPs suitable for use according to the invention comprises D-amino acids. In this case the order of the amino acid residues is reversed as compared to that found in the native class III SLRP.

It will be appreciated that derivatives of class III SLRPs suitable for use in accordance with the invention also include modified forms of class III SLRPs, or fragments thereof, in which the amino acid sequence has been altered compared to that of the corresponding native class III SLRP. These modified or variant forms of class III SLRPs may be produced by the addition, subtraction or substitution of one or more of the amino acid residues occurring in the native molecule. Suitable methods by which such addition, subtraction or substitution variants may be produced are well known to those skilled in the art, and are the subject of a great number of publications which provide details of experimental protocols which may be used. The nature of the amino acid substitutions to be made may be determined with reference to the effect that it is desired to achieve.

For example, as discussed above, modified forms of class III SLRPs may be designed to remove enzyme cleavage sites, thereby reducing enzymatic degradation and increasing half-life in vivo. There exists a wealth of publicly available information regarding amino acid motifs digested by different proteolytic enzymes and the skilled person would readily be able to recognise the occurrence of such motifs within native class III SLRP molecules. It is then a straightforward matter to produce modified versions of class III SLRPs in which amino acids are added, removed or replaced in order to disrupt the cleavage site.

Modified forms of class III SLRPs may also be produced such that they include amino acid sequences that may interact advantageously with the local environment to achieve a desired effect. For instance amino acid sequences may be introduced in order to promote binding of the modified class III SLRP to components of the extracellular matrix (ECM), thereby providing a reserve of the modified class III SLRP available in the vicinity of cells the activity of which it is wished to influence. For instance the skilled person may modify class III SLRPs so that they include amino acid sequences that promote adhesion of the modified molecules to ECM components associated with new blood vessel development.

Preferably modifications of class III SLRP sequence by addition or substitution of amino acids may be conservative modifications, such that the tertiary structure of the variant is not significantly altered from that of the native class III SLRP from which the variant is derived. There exists in the scientific literature a wealth of information to assist the skilled person in the production of modified peptides with conservative additions or substitutions, and the appropriate selection of amino acid residues to achieve such conservative modifications does not require the application of inventive activity on the part of the skilled practitioner.

Preferably a variant form of a class III SLRP may share at least 50% amino acid sequence identity with the corresponding portion of the native class III SLRP from which it is derived. More preferably the degree of identity may be at least 60%, or 70%, and most preferably the variant may share at least 80%, 90% or 95% homology with the corresponding portion of the sequence of the native peptide from which it is derived. The similarity of the amino acid sequence of variant forms of class III SLRPs to native molecules may readily be determined using freely available comparison software.

It will be appreciated that the agents according to the present invention may be used in a monotherapy (i.e. use of agents according to the invention alone to reduce new blood vessel formation or conditions characterised by excessive activity and/or migration of monocytes and/or macrophages).

Alternatively agents according to the invention may be used as an adjunct, or in combination with, known therapies able to inhibit blood vessel formation or the excessive activity and/or migration of monocytes and/or macrophages. The use of agents according to the invention in combination with other therapies may be preferred, since it is generally believed that redundancy in pro-angiogenic pathways (particularly those associated with tumour propagation) may require several pathways to be blocked in order to provide an optimal therapeutic effect.

Agents according to the invention may be used in combination with substances capable of inhibiting integrin function. Such substances may include neutralising antibodies capable of binding to integrins. Preferably the integrins the function of which is to be inhibited may be selected from the group comprising α4, α5, αV, β1 and β3.

The research conducted by the inventor represents the first medical use of class III SLRPs and derivatives thereof. Therefore according to a third aspect of the present invention there is provided the use of a class III SLRP as a medicament.

The class III SLRP may preferably be selected from the group comprising:

a) opticin (oculoglycan); or
b) epiphycan; or
c) mimecan (also known as osteoglycin); or
d) a chimeric molecule comprising elements of any of a) to c);
e) a modified form of any of a) to d); or
f) a biologically active fragment or derivative of any of a) to e).

Agents according to the invention may be combined in compositions having a number of different forms depending, in particular on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given.

Compositions comprising agents according to the invention may be used in a number of ways. For instance, systemic administration may be required in which case the compound may be contained within a composition which may, for example, be ingested orally in the form of a tablet, capsule or liquid. Alternatively the composition may be administered by injection into the blood stream. Injections may be intravenous (bolus or infusion) or subcutaneous (bolus or infusion). The compounds may be administered by inhalation (e.g. intranasally).

Compositions comprising agents according to the invention may be used to regulate blood vessel formation in the eye. Such compositions may be formulated for injection, either into the eye itself (e.g. intravitreal injection) or around the eye (e.g. peri-orbital injection). Alternatively, compounds may be formulated for topical application or irrigation of the eye, for instance in the form of eyedrops. Suitable compositions of formulations for injection or topical use will be well known to those skilled in the art.

Iontophoresis represents another route by which agents according to the invention may be delivered to a desired tissue. It is recognised that ocular iontophoresis (for example using the OcuPhor system produced by Iomed, Inc.) may provide a method by which agents may be introduced non-invasively into the interior of the eye.

Agents may also be incorporated within a slow or delayed release device. Such devices may, for example, be inserted on or under the skin, or other tissues (e.g. into the eye—and particularly the vitreous humour thereof; or into the vicinity of the eye) and the compound may be released over weeks or even months. Such devices may be particularly advantageous when long term treatment with an agent is required and which would normally require frequent administration (e.g. at least daily injection).

It will be appreciated that the amount of an agent that is required is determined by biological activity and bioavailability which in turn depends on the mode of administration, the physicochemical properties of the agent employed and whether the agent is being used as a monotherapy or in a combined therapy. The frequency of administration will also be influenced by the above-mentioned factors and particularly the half-life of the agent within the subject being treated.

Optimal dosages to be administered may be determined by those skilled in the art, and will vary with the particular agent in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of agents according to the invention and precise therapeutic regimes (such as daily doses of the compounds and the frequency of administration).

Generally, a daily dose of between 0.01 μg/kg of body weight and 1.0 g/kg of body weight of agents according to the invention may be used to inhibit angiogenesis, depending upon which specific agent is used. More preferably, the daily dose is between 0.01 mg/kg of body weight and 100 mg/kg of body weight.

Daily doses may be given as a single administration (e.g. a single daily injection or application of eye drops). Alternatively, the agent used may require administration twice or more times during a day. As an example, agents according to the invention may be administered as two (or more depending upon the severity of the condition) daily doses of between 10 μgs and 5000 mgs in eye drop form. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention according to the third aspect of the invention provides a pharmaceutical composition comprising a therapeutically effective amount of an agent according to the first or second aspects of the invention and optionally a pharmaceutically acceptable vehicle. In one embodiment, the amount of the agent is an amount from about 0.01 mg to about 800 mg. In another embodiment, the amount of the agent is an amount from about 0.01 mg to about 500 mg. In another embodiment, the amount of the agent is an amount from about 0.01 mg to about 250 mg. In another embodiment, the amount of the agent is an amount from about 0.1 mg to about 100 mg. In another embodiment, the amount of the agent is an amount from about 0.1 mg to about 20 mg.

Administration of 1-25 μg/ml opticin has been found to be particularly effective for inhibiting blood vessel formation (see the Examples). Opticin may be administered at a concentration of 1-10 μg/ml, and preferably opticin may be administered at a concentration of 1-25 μg/ml.

It will be appreciated that preferred doses of class III SLRPs other than opticin may be determined using similar methods to those employed in the Examples, but it is envisaged that administration of these compounds at a concentration of 1-25 μg/ml may achieve a therapeutic effect.

This invention provides a process for making a pharmaceutical composition comprising combining a therapeutically effective amount of an agent according to the invention and a pharmaceutically acceptable vehicle. A "therapeutically effective amount" is any amount of an agent according to the first aspect of the invention which, when administered to a subject inhibits angiogenesis. A "subject" is a vertebrate, mammal, domestic animal or human being.

A "pharmaceutically acceptable vehicle" is referred to herein is any physiological vehicle known to those of ordinary skill in the art useful in formulating pharmaceutical compositions.

In a preferred embodiment, the pharmaceutical vehicle is a liquid and the pharmaceutical composition is in the form of a solution. In another embodiment, the pharmaceutically acceptable vehicle is a solid and the composition is in the form of a powder or tablet. In a further embodiment, the pharmaceutical vehicle is a gel and the composition is in the may be in the form of a cream or the like.

A solid vehicle can include one or more substances which may also act as flavoring agents, lubricants, solubilizers, suspending agents, fillers, glidants, compression aids, binders or tablet-disintegrating agents; it can also be an encapsulating material. In powders, the vehicle is a finely divided solid that is in admixture with the finely divided active agent. In tablets, the active agent is mixed with a vehicle having the necessary compression properties in suitable proportions and compacted in the shape and size desired. The powders and tablets preferably contain up to 99% of the active agent. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active agent can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal, subcutaneous and particularly intraoccular injection. Sterile solutions can also be administered intravenously or used to irrigate the eye. The compounds may be prepared as a sterile solid composition that may be dissolved or suspended at the time of administration using sterile water, saline, or other appropriate sterile injectable medium. Vehicles are intended to include necessary and inert binders, suspending agents, lubricants, flavorants, sweeteners, preservatives, dyes, and coatings.

Agents according to the invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

Agents according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated by the skilled person that agents suitable for use according to the invention also include agents encoding class III SLRPs (as well as their derivatives). For example, possible agents include nucleic acid molecules encoding class III SLRPs. Such nucleic acids may preferably be administered in suitable vectors, for example the opticin cDNA inserted into a plasmid containing the E1/E3 deleted Ad5 genome, i.e. an adenoviral vector adenovirus). Such vectors may provide suitable agents for use in gene therapy.

A convenient way in which new blood vessel formation may be inhibited and/or monocyte/macrophage activation and/or migration prevented is to provide a therapeutically effective amount of such an agent in accordance with the invention at a site where such activity is required by means of gene therapy.

According to a fourth aspect of the present invention there is provided a delivery system for use in a gene therapy technique, said delivery system comprising a DNA molecule encoding for an agent in accordance with the invention, said DNA molecule being capable of being transcribed to lead to the expression of the chosen agent.

According to a fifth aspect of the present invention there is provided the use of a delivery system as defined in the preceding paragraph for use in the manufacture of a medicament for use in the inhibition of blood vessel formation.

According to a sixth aspect of the present invention there is provided a method of inhibiting blood vessel formation, the method comprising administering to a patient in need of treatment a therapeutically effective amount of a delivery system as defined for the fourth aspect of the invention.

Due to the degeneracy of the genetic code, it is clear that nucleic acid sequences encoding agents suitable for use in accordance with the invention may be varied or changed without substantially affecting the sequence of the product encoded thereby, to provide a functional variant thereof. An agent suitable for use in accordance with the invention must retain the ability to inhibit blood vessel formation, and to prevent activity and/or migration of monocytes and/or macrophages.

Suitable nucleotides encoding agents in accordance with the invention (including class III SLRPs, fragments and derivatives thereof) include those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid.

The delivery systems according to the invention are highly suitable for achieving sustained levels of an agent in accordance with the invention at a site where it is wished to inhibit blood vessel formation or the migration and/or activity of monocytes and/or macrophages over a longer period of time than is possible for most conventional delivery systems. For example, agents in accordance with the invention suitable for inhibiting blood vessel formation may be continuously expressed at the site where neovascularisation is to be inhibited by cells that have been transformed with the DNA molecule disclosed in the fourth aspect of the invention invention. Therefore, even if the agent in accordance with the invention has a very short half-life in vivo, therapeutically effective amounts of the agent may be continuously expressed from the treated tissue.

Furthermore, the delivery system of the invention may be used to provide the DNA molecule (and thereby the agent in accordance with the invention) without the need to use conventional pharmaceutical vehicles such as those required in ointments or creams that may otherwise be used in accordance with the invention.

The delivery system of the present invention is such that the DNA molecule is capable of being expressed (when the delivery system is administered to a patient) to produce an agent in accordance with the invention which directly or indirectly has activity for inhibiting blood vessel formation, and/or preventing activity and/or migration of monocytes and/or macrophages. By "directly" we mean that the product of gene expression per se has the required activity. By "indirectly" we mean that the product of gene expression undergoes or mediates (e.g. as an enzyme) at least one further reaction to provide an active agent having the requisite activity.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors may be designed such that the vector will autonomously replicate in the nucleus of the cell. In this case, elements that induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one that becomes incorporated in the DNA of cells of the subject being treated. Undifferentiated cells may be stably transformed leading to the production of genetically modified daughter cells. When this is the case, regulation of expression in the subject may be required e.g. with specific transcription factors, gene activators or more preferably with inducible promoters which transcribe the gene in response to a signal specifically found at a site of new blood vessel formation. Alternatively, the delivery system may be designed to favour unstable or transient transformation of differentiated cells in the subject being treated. In this instance, regulation of expression may be less important because expression of the DNA molecule will stop when the transformed cells die or stop expressing the protein (ideally when the requisite inhibition of blood vessel formation has been effected).

The delivery system may provide the DNA molecule to a subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly (for instance either topically or by injection) to a site where blood vessel formation is to be inhibited.

The agent in accordance with the invention expressed from the DNA molecule may be a class III SLRP, or a biologically active fragment or derivative thereof.

Methods of the invention may be put into practice by inducing increased cellular expression of an agent in accordance with the invention, which may then inhibit blood vessel formation or macrophage and/or monocyte activity and/or migration. Such therapeutic expression of an agent in accordance with the invention may be achieved by increasing naturally occurring expression of the agent (for example the natural expression of a naturally occurring class III SLRP), or by inducing unnatural expression of the agent (e.g. induction of class III SLRP expression by cells that do not naturally express class III SLRPs) or by inducing over-expression of the agent. It will be appreciated that an increase in endogenous expression of class III SLRPs such as opticin may readily be achieved by the administration of an agent capable of increasing the transcription of the gene encoding opticin.

According to a seventh aspect of the invention there is provided a method of screening a test compound for its ability to inhibit blood vessel formation, the method comprising:

i) assessing the degree of binding between a class III SLRP and a substrate of the class III SLRP in the absence of the test compound,
ii) assessing the degree of binding between the class III SLRP and the substrate in the presence of the test compound,
iii) comparing the degree of binding occurring in step i) with the degree of binding occurring in step ii);

wherein a test compound is able inhibit blood vessel formation if the degree of binding occurring in step ii) is less than the degree of binding occurring in step i).

In accordance with a eighth aspect of the invention there is provided a method of screening a test compound for its ability to inhibit activity and/or migration of monocytes and/or macrophages, the method comprising:

i) assessing the degree of binding between a class III SLRP and a substrate of the class III SLRP in the absence of the test compound,
ii) assessing the degree of binding between the class III SLRP and the substrate in the presence of the test compound,
iii) comparing the degree of binding occurring in step i) with the degree of binding occurring in step ii);

wherein a test compound is able inhibit activity and/or migration of monocytes and/or macrophages if the degree of binding occurring in step ii) is less than the degree of binding occurring in step i).

The substrate may be heparin or heparan sulphate, or a growth factor, particularly an angiogenic growth factor such as VEGF, FGF. Alternatively the substrate may be a cellular receptor bound by class III SLRPs. Examples of such receptors include the cellular receptors for VEGF and FGF.

It will be appreciated that other agents having the same cellular receptor-binding profile as class III SLRPs, such as opticin, may be expected to have similar biological effects to those exhibited by class III SLRPs. Thus, in a further aspect of the present invention there is provided the use of an agent having substantially the same receptor-binding profile as a class III SLRP in the manufacture of a medicament for the inhibition of blood vessel formation. Agents having substantially the same receptor-binding profile as a class III SLRP may also be used in the manufacture of a medicament for the prevention and/or treatment of conditions characterised by excessive activity and/or migration of monocytes and/or macrophages.

It will also be appreciated that the recognition of the importance of the receptor-binding profile of class III SLRPs in mediating the biological behaviour of these molecules provides a means by which agents able to mimic class III SLRP activity (i.e. by inhibiting blood vessel formation or the migration and/or activation of monocytes and/or macrophages) may be identified.

Accordingly, the invention provides a method of screening a test compound for the ability to mimic class III SLRP activity, the method comprising comparing the receptor-binding profile of the test compound with the receptor-binding profile of a class III SLRP, wherein having substantially the same receptor-binding profile as a class III SLRP indicates that the class III SLRP is able to mimic class III SLRP activity.

The characteristic receptor-binding profiles of class III SLRPs may be readily determined using experimental methods and protocols well known to those skilled in the art.

EXAMPLE 1

Effects of Opticin on Vascular Endothelial Cell Proliferation

Proliferation assays were undertaken with bovine aortic endothelial cells (BAEC) (method described in Slevin M, Kumar S, Gaffney J. Angiogenic oligosaccharides of hyaluronan induce multiple signaling pathways affecting vascular endothelial cell mitogenic and wound healing responses. J. Biol. Chem. 2002. 277: 41046-59) in the presence of growth factors and recombinant opticin. The full-length recombinant opticin was generated using the pCEP-Pu vector in human embryonic kidney cells (Le Goff et al. Characterization of opticin and evidence of stable dimerisation in solution. J. Biol. Chem. 2003. 278: 45280-7). The opticin was purified from conditioned media using a combination of ion-exchange and lectin affinity chromatography. For the proliferation assays the BAEC were seeded in triplicate in 6 well plates at a concentration of $2\times10^4$/ml. After attachment they were cultured in serum poor medium containing 2.5% fetal calf serum. In some wells the cells were pre-incubated with opticin 0.1-10 μg/ml for one hour prior to the addition of growth factors including FGF-2, FGF-1 (both at 25 ng/ml) or VEGF isoforms (at 10 ng/ml). The cells were then incubated for a further 72 hours. At 72 hours the cells were washed, detached with trypsin and counted on a Coulter counter.

Control experiments showed that opticin is not toxic to the cells at the concentrations used in these experiments (data not shown). Mean values are shown in FIGS. 3 to 6, which illustrate the effect of opticin on the proliferation of endothelial cells induced by several pro-angiogenic growth factors.

As shown in FIG. 3, 1=Control (i.e. cells with no growth factor or opticin added), 2=Control+10 μg/ml of opticin, 3=FGF-2 alone , 4=FGF-2+0.1 μg/ml of opticin, 5=FGF-2+1 μg/ml of opticin, 6=FGF-2+10 μg/ml of opticin, 7=FGF-2+25 μg/ml of opticin. With increasing concentrations of opticin the FGF-2 induced cellular proliferation is decreased towards baseline (control) levels. Concentrations of between 1 and 25 μg/ml caused a significant reduction in BAEC proliferation when compared to FGF-2 alone. Opticin at 25 μg/ml caused a >95% inhibition of FGF-2 induced BAEC proliferation.

As shown in FIG. 4, the effects of opticin at 10 μg/ml on BAEC proliferation induced by FGF-2 and FGF-1 are compared. The presence of opticin reduces the level of proliferation induced by both growth factors to approximately control levels; thereby illustrating that opticin is as effective at inhibiting FGF-1 as FGF-2 induced proliferation.

As shown in FIG. 5, 1=Control, 2=VEGF, 3=VEGF+1 μg/ml of opticin; 4=VEGF +10 μg/ml of opticin. With increasing concentrations of opticin the VEGF induced cellular proliferation is decreased towards baseline (control) levels Both 1 μg/ml and 10 μg/ml of opticin caused a significant reduction in BAEC proliferation when compared to VEGF alone, and 10 μg/ml of opticin caused a >90% inhibition of proliferation.

As shown in FIG. 6, the effects of opticin at 10 μg/ml on BAEC proliferation induced by $VEGF_{164}$ and $VEGF_{120}$ are compared. The presence of opticin reduces the level of proliferation induced by both growth factors to approximately control levels; thereby illustrating that opticin is as effective at inhibiting $VEGF_{120}$ as $VEGF_{164}$ induced proliferation.

It will be appreciated that inhibition of the proliferation of endothelial cells indicates that agents according to the present invention will have efficacy for inhibiting blood vessel formation.

EXAMPLE 2

Effects of Opticin on Bovine Aortic Endothelial Cell (BAEC) Sprout Formation Induced by FGF-2 and VEGF The ability of confluent BAEC to form "sprouts" of 'tube-like' capillaries on plates coated with 0.1% gelatin/PBS was investigated in the presence of opticin (based on method described in Canfield AE and Schor AM. Evidence that tenascin and thrombospondin-1 modulate sprouting of endothelial cells. J Cell Sci. 1995. 108:797-809). Such sprouting activity provides an in vitro model of new blood vessel formation.

Briefly, triplicate coated wells of a 6 well plate containing just-confluent BAEC were placed in 2.5% FCS-DMEM and treated with opticin for 1 hr (0.1-10 μg/ml) before adding FGF-2 (25 ng/ml) or VEGF (10 ng/ml) and then allowing to incubate for 12 days.

Control wells were treated with vehicle only (PBS). At the end of the experiment, 5 random fields from each well were photographed by phase-contrast microscopy (FIG. 7) and the area covered by sprouts determined by image analysis.

In FIG. 8, a graphical representation of mean areas covered by the sprouts is shown. The "Control" values represent the % of coverage by sprouting cells after 12 days with no added mitogen or opticin. The bars labelled "Opticin" show the effects of adding opticin alone upon sprout formation, and illustrate there was no significant difference when compared to the controls. Next the effects of adding growth factor alone are shown. The final three bars show the effect of adding growth factor and increasing concentrations of opticin. Bars are marked with an asterisk where there was a significant decrease in sprout formation compared with growth factor alone. At 10 μg/ml, opticin reduced the FGF-2-induced cell sprouting by 73% and the VEGF-induced sprouting by 70%, illustrating the effectiveness of the Class III SLRP opticin in reducing new blood vessel formation.

EXAMPLE 3

Effects of Opticin on Bovine Aortic Endothelial Cell (BAEC) Migration Induced by FGF-2 and VEGF The cell-layer wounding assay used is described in: Slevin M, Kumar S, Gaffney J. Angiogenic oligosaccharides of hyaluronan induce multiple signaling pathways affecting vascular endothelial cell mitogenic and wound healing responses. J. Biol. Chem. 2002. 277: 41046-59. BAECs were cultured on plastic coverslips until confluent and then placed in medium containing 5% FCS. After a further 24 hrs the coverslips were washed in PBS and then the cellular layer was wounded with a razor blade. Opticin (0.1-10

μg/ml) was added to some of the wells and allowed to incubate for a further 1 hr. FGF-2 (25 ng/ml) or VEGF (10 ng/ml) were then added to test wells and the plate incubated at 37° C. for 24 hrs. After incubation, the coverslips were rinsed in PBS and fixed in 100% ethanol. Movement of cells into the denuded area was quantified using a computerized image analysis system. The area was then converted to give mean % coverage from 3 identically treated coverslips.

In FIG. 9, graphical analysis of the denuded areas recovered by BAECS. The "Control" value represents mean area covered by the cells after 24 hrs incubation with no added mitogen or opticin. The bar labelled "Opticin" illustrates that addition of opticin alone has no significant effect upon cell migration when compared to the control untreated cells.

The bars labelled "VEGF" and "FGF-2" show the effect of these factors (added at concentrations of 10 ng/ml and 25 ng/ml respectively) on cell migration.

The bars labelled "VEGF+Opticin" and "FGF-2 +Opticin" illustrate the effect of the addition of 10 μg/ml opticin on growth factor-induced cell migration. The class III SLRP opticin reduced the VEGF-induced cell movement by 53% and the FGF-2-induced cell migration by 86%. This reduction in endothelial cell migration illustrates the ability of class III SLRPs to inhibit blood vessel formation.

It will be appreciated in the light of the results described above that class III SLRPs such as opticin may be used to prevent the migration of endothelial cells in a range of contexts.

EXAMPLE 4

Effects of Opticin on $VEGF_{164}$ and FGF-2 Induced ERK Phosphorylation

Here the effects of opticin on signalling through the MAPK pathway were investigated as this pathway plays a key role in vascular endothelial cell proliferaton and migration. Semi-confluent BAEC cultured in 6 well plates in SPM for 48 h were pre-incubated for one hour with opticin at 10 μg/ml before the addition of either FGF-2 (25 ng/ml) or $VEGF_{164}$ (10 ng/ml). After between five and twenty minutes incubation total cell lysates were collected in radioimmunoprecipitation (RIPA) buffer, containing 10 mM Tris HCl, (pH 7.5), 50 mM NaCl, 0.5% w/v sodium deoxycholate, 0.5% v/v Nonidet P40, 0.1% w/v SDS, 1 mM $Na_3VO_4$ and 5 μg/ml aprotinin (Vainnika et al, 1994). Samples were then centrifuged (10,000 g for 15 min at 4° C.) to remove insoluble debris, and stored at −70° C. until use. Protein concentration of the cell lysates was determined using a modification of the Bradford assay (Bio-Rad, California, USA) and equal quantities of protein (15 μg) were mixed with 2× Laemmli sample buffer, vortex mixed and boiled in a water bath for 15 min. SDS-PAGE was undertaken using 4-12% Bis-Tris gradient gels (Invitrogen) with the MES system according to manufacturer's instructions. Samples were then subjected to Western blotting with antibodies that recognise phosphorylated ERK-1 and 2, total ERK-2 and α-actin.

As shown in FIG. 10, Western blots demonstrate that pre-incubation of BAEC with opticin reduced the ability of both $VEGF_{164}$ and FGF-2 to induce ERK1/2 phosphorylation in $VEGF_{164}$ and FGF-2 treated cells. That lanes of the gel had been loaded equally was confirmed by probing with antibodies that recognise total ERK-2 and α-actin.

EXAMPLE 5

Chick Chorioallantoic Membrane (CAM) Assay

CAM assays were performed according to accepted protocols. Briefly, pellets containing the angiogenic growth factor FGF-2, either in the presence or absence of 1 μg of opticin, were placed in contact with the chorioallantoic membranes of day 8 eggs. After 2 days the number of blood vessels growing towards the pellet was counted and the number of blood vessels present analysed.

As shown in FIG. 11, the exemplar images clearly illustrate that fewer new blood vessels have grown towards the pellet containing FGF-2 and opticin as compared to the pellet containing FGF-2 alone. This clearly establishes that the class III SLRP opticin is able to dramatically reduce new blood vessel formation which otherwise occurs in vivo in response to the activity of angiogenic growth factors.

EXAMPLE 6

Opticin Interacts with Integrins Involved in Angiogenesis

Cell-spreading assays were undertaken using the A375-SM human melanoma cells, which express a wide variety of integrins. The cells were plated on recombinant bovine opticin or control substrates including BSA (negative control), VCAM and 50K, a 50-kDa fibronectin fragment (positive controls). The cells were allowed to spread for 1 hr and during that time spreading was less than 5% on BSA; illustrating that there was no detectable spreading on endogenously produced ligand in this time-frame.

As shown in FIG. 12, cell spreading on opticin at different concentrations showed a dose-response effect and reached a maximum spreading of ~30% when opticin was coated at a concentration of 100 μg/ml. The dose-response curves (below) were used to determine the optimum coating concentrations of the ligands for inhibition assays i.e. 35 μg/ml for opticin, 10 μg/ml for VCAM and 10 μg/ml for 50K.

As shown in FIG. 13, cell spreading assays were undertaken in conjunction with function-blocking integrin antibodies. Graph shows percentage cell spreading plotted against different antibody combinations. H120 is an irrelevant antibody used as a negative control. Combinations of antibodies including α4, α5 and αV or β1 and β3 antibodies almost completely inhibited spreading and taken together these results may suggest that opticin interacts with α4β1, α5β1, αVβ3. The α5β1 and αVβ3 integrins are expressed by vascular endothelial during angiogenesis and play key roles in the process. Although the inventors do not wish to be constrained by any hypothesis, it is believed that the interaction of class III SLRPs such as opticin with these angiogenic integrins may help prevent cell adhesion, spreading and migration required for angiogenic sprouting, thereby preventing new blood vessel formation. In addition, opticin interactions with these integrins are believed to cause outside-to-inside signalling through the integrins leading to downregulation of signalling through growth factor receptors including the VEGF and FGF receptors.

EXAMPLE 7

Solid Phase Binding Assays Analysing the Binding of Opticin to FGF-1, FGF-2, $VEGF_{164}$, $VEGF_{121}$, and Their Receptors The soluble extracellular domains of the receptors were obtained from R&D Systems Europe Ltd.

i) Opticin Binding Assays

Briefly, growth factor receptors (FGF-R1, FGF-R2, VEGF-R1 and VEGF-R2—see FIG. 14) growth factors (FGF-2, FGF-1, $VEGF_{164}$, $VEGF_{120}$, —see FIG. 15) were coated at 2 μg/ml on 96-wells plates. The wells were then blocked with 1% BSA. Opticin at varying concentrations in PBS was added to the wells and incubated for 2 hrs. Bound opticin was detected with an opticin-specific antibody.

As shown in FIG. 14, opticin bound to the VEGF-R1 and FGF-R2 in a dose-response dependent manner, but did not bind to VEGF-R2 or FGF-R1. An apparent Kd of 21 nM was obtained for VEGF-R1 binding, but as saturation was not reached for FGF-R2 binding, it was not possible to derive a Kd.

The ability of opticin to bind to VEGF-R1 and to FGF-R2 suggests that it is this binding that is important in mediating opticin's activity as it relates to both pathological angiogenesis and monocyte and/or macrophage activity/and or migration. Opticin's binding to these receptors may prevent the binding of their biologically active ligands, thereby reducing the level of activity and/or migration that such ligands are able to induce.

As shown in FIG. 15, opticin bound to FGF-2 and $VEGF_{164}$ in a dose-response dependent manner, but it did not bind to FGF-1 of $VEGF_{120}$. Apparent dissociation constant (Kd) values of 34 nM for FGF-2 and 42 nM for $VEGF_{164}$ were derived.

ii) Competition Assays

As opticin did not bind to VEGF-R2 and FGF-R1 in the solid-phase experiments, the inventors investigated whether opticin inhibited the interactions of these receptors with $VEGF_{164}$ and FGF-2 respectively. Competition assays were performed by coating the wells with (A) FGF-R1 or (B) VEGF-R2 at 2 μg/ml, then after blocking with 1% BSA, the wells were incubated with 0.2 μg/ml of (A) FGF-2 or (B) $VEGF_{164}$ mixed with varying concentrations of opticin. Growth factor binding to their receptors was detected with specific antibodies.

As shown in FIG. 16, opticin inhibits the interaction between FGF-2 and FGF-R1 (A) and $VEGF_{165}$ to VEGF-R2 (B) in a dose-dependent manner. Therefore in both cases the binding of opticin to the growth factor inhibits the interaction of the growth factor with its receptor.

iii) Conclusions

The results show that class III SLRPs are able to inhibit endothelial cell proliferation, migration and sprout formation. These are all essential elements of the process of angiogenesis so the skilled person will appreciate that Class III SLRPs inhibit angiogenesis. Furthermore, opticin inhibits angiogenesis in the CAM assay thus providing in-vivo evidence for the anti-angiogenic effects of opticin.

The class III SLRP opticin inhibits processes involved in angiogenesis through several mechanisms. It inhibits the pro-angiogenic actions of the growth factors FGF-1, FGF-2, $VEGF_{165}$ and $VEGF_{121}$. In the cases of $VEGF_{165}$ and FGF-2 opticin has a direct action by binding to the growth factors and inhibiting their interactions with their receptors. However, opticin also inhibits angiogenesis through other mechanisms, as it is effective at inhibiting the stimulatory actions of growth factors that it does not bind including FGF-1 and $VEGF_{121}$. Other mechanisms through which opticin inhibits angiogenesis are through direct growth factor receptor interactions with VEGFR-1 and FGFR-2, thereby reducing biological activity mediated by these receptors and by interacting with integrins involved in angiogenesis including αVβ3 and α5β1 thereby affecting integrin-ligand binding and/or outside-to-inside signalling and indirectly suppressing signalling through growth factor receptors.

The invention claimed is:

1. A method of inhibiting blood vessel formation in a subject, said method comprising administering to a subject an effective amount of a class III small leucine rich protein (SLRP) to inhibit blood vessel formation, wherein the blood vessel formation is inhibited.

2. The method of claim 1, wherein the class III SLRP is selected from the group consisting of opticin, epiphycan, mimecan, chimeric molecules comprising opticin, epiphycan, mimecan, and fragments of opticin, epiphycan, mimecan, wherein said fragments inhibit blood vessel formation.

3. A method of treating a pathological condition associated with new blood vessel formation, said method comprising administering to a subject an effective amount to a class III small leucine rich protein (SLRP) to inhibit blood vessel formation, wherein the blood vessel formation is inhibited and the pathological condition is treated.

4. The method of claim 3, wherein the class III SLRP is selected from the group consisting of opticin, epiphycan, mimecan, chimeric molecules comprising opticin, epiphycan, or mimecan, and fragments of opticin, epiphycan, or mimecan, wherein said fragments inhibit blood vessel formation.

5. The method of claim 3, wherein the pathological condition is selected from cancer, psoriasis, wound healing, and an inflammatory condition.

6. The method claim 5, wherein the inflammatory condition is selected from uveitis, arthritis and a combination thereof.

7. The method of claim 3, wherein the pathological condition is a vasoproliferative retinopathy of the eye.

8. The method of claim 7, wherein the vasoproliferative retinopathy is selected from proliferative diabetic retinopathy, 'wet' macular degeneration, choroidal neovascularization and persistent primary hyperplastic vitreous.

9. A method of inhibiting undesirable endothelial cell proliferation or migration, comprising contacting an endothelial cell with an amount of a class Ill small leucine rich protein (SLRP) sufficient to inhibit or reduce endothelial cell proliferation or migration.

10. The method of claim 9, wherein the class III SLRP is selected from the group consisting of opticin, epiphycan, mimecan, chimeric molecules comprising opticin, epiphycan, or mimecan, and fragments of opticin, epiphycan, or mimecan, wherein said fragments inhibit endothelial cell proliferation or migration.

* * * * *